United States Patent
Murray, III

(10) Patent No.: US 7,189,215 B2
(45) Date of Patent: *Mar. 13, 2007

(54) CATHETER WITH FULL-LENGTH CORE WIRE SHAFT FOR CORE WIRE INTERCHANGEABILITY

(75) Inventor: Robert J Murray, III, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 135 days.

This patent is subject to a terminal disclaimer.

(21) Appl. No.: 10/641,003

(22) Filed: Aug. 15, 2003

(65) Prior Publication Data

US 2004/0092867 A1 May 13, 2004

Related U.S. Application Data

(63) Continuation-in-part of application No. 10/291,625, filed on Nov. 12, 2002.

(51) Int. Cl.
*A61M 29/00* (2006.01)
*A61M 31/00* (2006.01)
*A61M 37/00* (2006.01)

(52) U.S. Cl. .................. 604/103.09; 604/103.04; 606/194

(58) Field of Classification Search ............. 604/96.01, 604/103, 103.04, 103.09
See application file for complete search history.

(56) References Cited

U.S. PATENT DOCUMENTS

| 4,723,936 A * | 2/1988 | Buchbinder et al. ..... 604/95.01 |
| 4,808,164 A * | 2/1989 | Hess ................. 604/95.01 |
| 4,927,413 A * | 5/1990 | Hess ................. 604/96.01 |
| 4,960,410 A | 10/1990 | Pinchuk |
| 4,998,917 A | 3/1991 | Gaiser et al. |
| 5,040,548 A | 8/1991 | Yock |
| 5,141,518 A * | 8/1992 | Hess et al. ................. 606/194 |
| 5,147,317 A * | 9/1992 | Shank et al. ........... 604/164.13 |
| 5,370,655 A | 12/1994 | Burns |
| 5,429,597 A * | 7/1995 | DeMello et al. ............ 604/509 |
| 5,484,409 A | 1/1996 | Ellis et al. |
| 5,573,520 A | 11/1996 | Schwartz et al. |
| 5,599,319 A | 2/1997 | Stevens |

(Continued)

FOREIGN PATENT DOCUMENTS

| EP | 0563759 | 10/1993 |
| WO | 0228466 | 4/2002 |

*Primary Examiner*—Kevin C. Sirmons
*Assistant Examiner*—Andrew Gilbert

(57) ABSTRACT

A catheter to be used without a guidewire which includes a support wire shaft formed of metal, a balloon mounted on a distal portion of the catheter, and an inflation shaft for inflating the balloon, wherein a core wire may be interchangeably inserted into the support wire shaft when the catheter is within a human body to change the stiffness and improve control thereof. In one embodiment, the portion of the support wire shaft that extends just proximal of, through and distal of the balloon is formed entirely of a metal wound coil. The flexibility characteristics of this support wire shaft can be controlled by varying the pitch of the wound coil and the thickness of the wire or ribbon it is made from. An overjacket is also provided on the metal wound coil portion to hold pressure within the inflation lumen and provide a suitable material for bonding a distal end of the balloon to the support wire shaft.

7 Claims, 25 Drawing Sheets

U.S. PATENT DOCUMENTS

| | | |
|---|---|---|
| 5,807,355 A | 9/1998 | Ramzipoor et al. |
| 5,961,510 A | 10/1999 | Fugoso et al. |
| 6,048,338 A | 4/2000 | Larson et al. |
| 6,059,713 A | 5/2000 | Ehr et al. |
| 6,102,890 A | 8/2000 | Stivland et al. |
| 6,193,686 B1 * | 2/2001 | Estrada et al. ......... 604/103.09 |
| 6,203,558 B1 | 3/2001 | Dusbabek et al. |
| 6,270,504 B1 | 8/2001 | Lorentzen Cornelius et al. |
| 6,306,124 B1 | 10/2001 | Jones et al. |
| 6,361,529 B1 | 3/2002 | Goodin et al. |
| 2001/0037085 A1 | 11/2001 | Euteneuer et al. |
| 2002/0038103 A1 | 3/2002 | Estrada et al. |

* cited by examiner

B-B

CATHETER WITH FULL-LENGTH CORE WIRE SHAFT FOR CORE WIRE INTERCHANGEABILITY

CROSS-REFERENCE TO RELATED APPLICATIONS

This application is a continuation-in-part of co-pending U.S. application Ser. No. 10/291,625, filed Nov. 12, 2002, incorporated by reference herein in its entirety.

BACKGROUND OF THE INVENTION

1. Field of the Invention

The present invention relates to catheters, and more particularly to catheters with variable stiffness that may be used with an interchangeable core wire.

2. Background of the Invention

Cardiovascular disease, including atherosclerosis, is the leading cause of death in the U.S. The medical community has developed a number of methods and devices for treating coronary heart disease, some of which are specifically designed to treat the complications resulting from atherosclerosis and other forms of coronary arterial narrowing.

One method for treating atherosclerosis and other forms of coronary narrowing is percutaneous transluminal coronary angioplasty, commonly referred to as "angioplasty" or "PTCA". The objective in angioplasty is to enlarge the lumen of the affected coronary artery by radial hydraulic expansion. The procedure is accomplished by inflating a balloon of a balloon catheter within the narrowed lumen of the coronary artery. Radial expansion of the coronary artery occurs in several different dimensions, and is related to the nature of the plaque.

Soft, fatty plaque deposits are flattened by the balloon, while hardened deposits are cracked and split to enlarge the lumen. The wall of the artery itself is also stretched when the balloon is inflated.

One or multiple dilations may be necessary to effectively dilate the artery. In many instances, multiple dilations using multiple "over-the-wire" balloon catheters having balloons with increasingly larger diameters maybe required. An over-the-wire catheter is one where a guidewire lumen is provided so that the catheter can be guided to the stenosis site by running the entire catheter length along the guidewire.

Conventional angioplasty guidewire typically include a proximal shaft, an intermediate section and a flexible distal tip. The proximal shaft comprises a solid wire or a solid wall tube. The proximal shaft primarily functions to guide and support a catheter, and to smoothly transmit rotation from the proximal end to an intermediate section.

The intermediate section of the guidewire extends axially from the proximal shaft and generally comprises a tapered core wire surrounded by a coiled spring and typically has more flexibility than the proximal shaft. Like the proximal shaft, the intermediate section must assist in guiding the catheter and smoothly transmitting rotation. However, some degree of flexibility in the intermediate section is desirable to conform the catheter to the curvature of the aortic arch and the coronary arteries.

A flexible distal tip mounts to the end of the intermediate portion and projects axially from the intermediate section. Typically, the flexible distal tip accepts a pre-formed curved shape resembling a "J". The curved tip tends to steer the guide wire in the direction of the hook.

In a typical procedure, a physician will first insert and advance a guidewire to the stenosis site. An initial over-the-wire balloon dilation catheter having a fairly small diameter balloon is then passed over the guidewire to the site and the balloon is inflated to partially dilate the vessel. The balloon is then deflated and the catheter withdrawn. Balloon catheters having progressively larger balloons are then advanced to the stenosis along the guidewire, inflated, deflated, and then withdrawn in succession to sufficiently enlarge the lumen of the artery.

Balloon catheters include an inflation lumen through which a fluid can be forced to pressurize the balloon. As such, balloon catheters having a full-length guidewire lumen, must have at least two lumens. Catheters having more than one lumen are commonly referred to as "dual-lumen" or "multi-lumen" catheters.

Multi-lumen catheters have cross-sections in a variety of shapes. FIGS. 1 and 2 are examples of prior art dual lumen catheter cross-sections. FIG. 1 is a cross-section of coaxial catheter 100. Coaxial catheter 100 includes inner tube 102 and outer tube 104. Inner tube 102 defines an inner lumen or guidewire lumen 108 adapted to receive guidewire 106. Annular inflation lumen 110 is defined between inner tube 102 and outer tube 104, and is in fluid communication with an interior of a dilatation balloon (not shown).

In use, a guidewire is introduced into a coronary artery and is steered by manipulation of its proximal end, while being observed under a fluoroscope, until the guidewire passes through a stenosis in the artery. Once the guidewire is in place, a balloon dilatation catheter is advanced over the guidewire, being thus guided directly to the stenosis so as to place the balloon within the stenosis. Once so placed, the balloon is inflated under substantial pressure to dilate the stenosis.

The anatomy of coronary arteries varies widely from patient to patient. Often a patient's coronary arteries are irregularly shaped and highly tortuous. The tortuous configuration of the arteries may present difficulties to the physician in proper placement of the guidewire, and advancement of the catheter to the site of the stenosis. A highly tortuous coronary anatomy typically will present considerable resistance to advancement of the catheter over the guidewire.

With some types of catheter construction, the increased resistance may cause a tendency for portions of the catheter to collapse or buckle axially. For example, in a catheter having a shaft formed from inner and outer coaxial tubes, such as is shown in FIG. 1, and a balloon mounted to the distal ends of the tubes, there may be a tendency for the tubes to "telescope" when presented with an increase in resistance. The telescoping of the tubes tends to draw the ends of the balloon together slightly, but sufficiently to permit the balloon to become bunched-up as it is forced through the stenosis. The bunching-up of the balloon makes it more difficult for the balloon to cross the stenosis.

Additionally, it is sometimes necessary for the physician to place a torque load on the guidewire in an effort to overcome resistance encountered in a vessel. Torque is also used to steer the guidewire through separate passages and bifurcation of the anatomy. A torque load applied to a coaxial catheter can cause the outer tube to twist, while the inner tube remains stationary, causing a rotation of the tubes relative to one another.

FIG. 2 shows a cross-sectional view of a non-coaxial dual-lumen catheter 200. An inflation lumen 202 is in fluid communication with an interior of a dilatation balloon (not shown). A guidewire lumen 204 is defined at least in part by an inner tubular member 206 which extends the entire length of the catheter body. A guidewire 208 is shown within guidewire lumen 204. As explained above, catheter 200 is slid over guidewire 208 through a tortuous blood vessel.

Catheter 200 does not experience telescoping of the tubes upon increased resistance or twisting of the tubes relative to each other when a torque load is applied. However, once catheter 200 is selected and tracked over a guidewire inserted in a patient's vasculature, the physician may discover that the catheter has insufficient stiffness at its distal end to cross a lesion. This limits the use of such catheters in many procedures. Accordingly, a need exists for a physician to be able to change (for example, to increase) the stiffness of a catheter being used to traverse a particularly difficult lesion without removing the catheter from the patient's vasculature.

BRIEF SUMMARY OF THE INVENTION

The present invention is directed to a catheter that substantially obviates one or more of the problems and disadvantages of the related art.

There is provided a dilatation catheter including a hollow support wire shaft formed of metal or plastic, such that a core wire may be interchangeably inserted into the support wire shaft when the catheter is within a body lumen. A balloon is mounted on a distal portion of the catheter and an inflation shaft is coupled to the balloon.

A proximal portion of the support wire shaft is arranged side-by-side with a proximal portion of the inflation shaft. However, a transition area is provided wherein a distal portion of the support wire shaft proximal of the balloon becomes coaxial with a distal portion of the inflation shaft where the inflation shaft is in fluid communication with the balloon.

In one embodiment of the invention, the support wire shaft is bonded to the inflation shaft over a substantial portion of their proximal length. In another embodiment, a jacket encapsulates and secures a substantial portion of the proximal length of the support wire shaft and the inflation shaft.

A distal portion of the support wire shaft that extends distally of the balloon is constructed to be more flexible than a portion of the support wire shaft proximal of the balloon. In one embodiment, a metal coil forms a distalmost portion of the support wire shaft distal of the balloon and imparts additional flexibility and maneuverability to the catheter. In another embodiment, a portion of the support wire shaft includes a helical slit to gradually decrease stiffniess of the support wire shaft as it extends just proximal of, through and distal of the balloon. A metal coil may then be utilized at a distalmost end of the helical slit portion of the support wire shaft to further increase the flexibility and maneuverability of the catheter thereof. In an alternate embodiment, the portion of the support wire shaft that extends just proximal of, through and distal of the balloon is formed entirely of a metal coil. The flexibility characteristics of this support wire shaft can be controlled by varying the pitch of the coil and the thickness of the wire or ribbon it is made from. An overjacket is also provided to hold pressure within the inflation lumen and provide a suitable material for bonding a distal end of the balloon to the support wire shaft.

A dilatation catheter according to the present invention also includes a core wire locking mechanism that is used to secure a core wire relative to the support wire shaft in which it is inserted. However, a catheter in accordance with the present invention is constructed to be sufficiently stiff to traverse a tortuous path within a patient's vasculature without a core wire inserted within the support wire shaft.

Additional features and advantages of the invention will be set forth in the description which follows, and in part will be apparent from the description, or may be learned by practice of the invention. The advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

The embodiments of the present invention are now described with reference to the figures where like reference numbers indicate identical or functionally similar elements. While specific materials and method steps are discussed, it should be understood that this is done for illustrative purposes only. A person skilled in the relevant art will recognize that other materials or method steps can be used.

Figure 1:
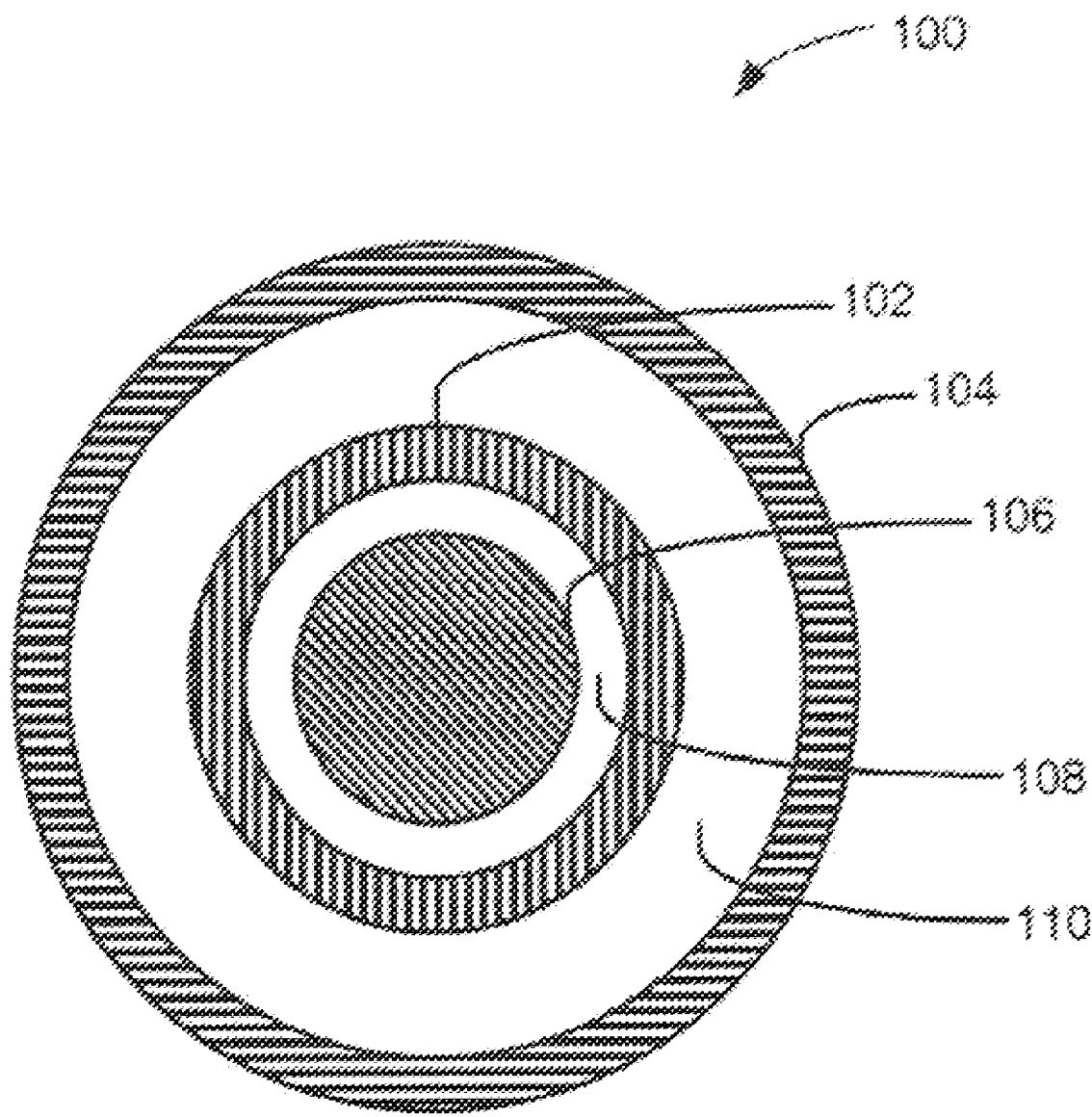
FIG. 1 is a cross-sectional view of a prior art coaxial catheter.
Figure 2:
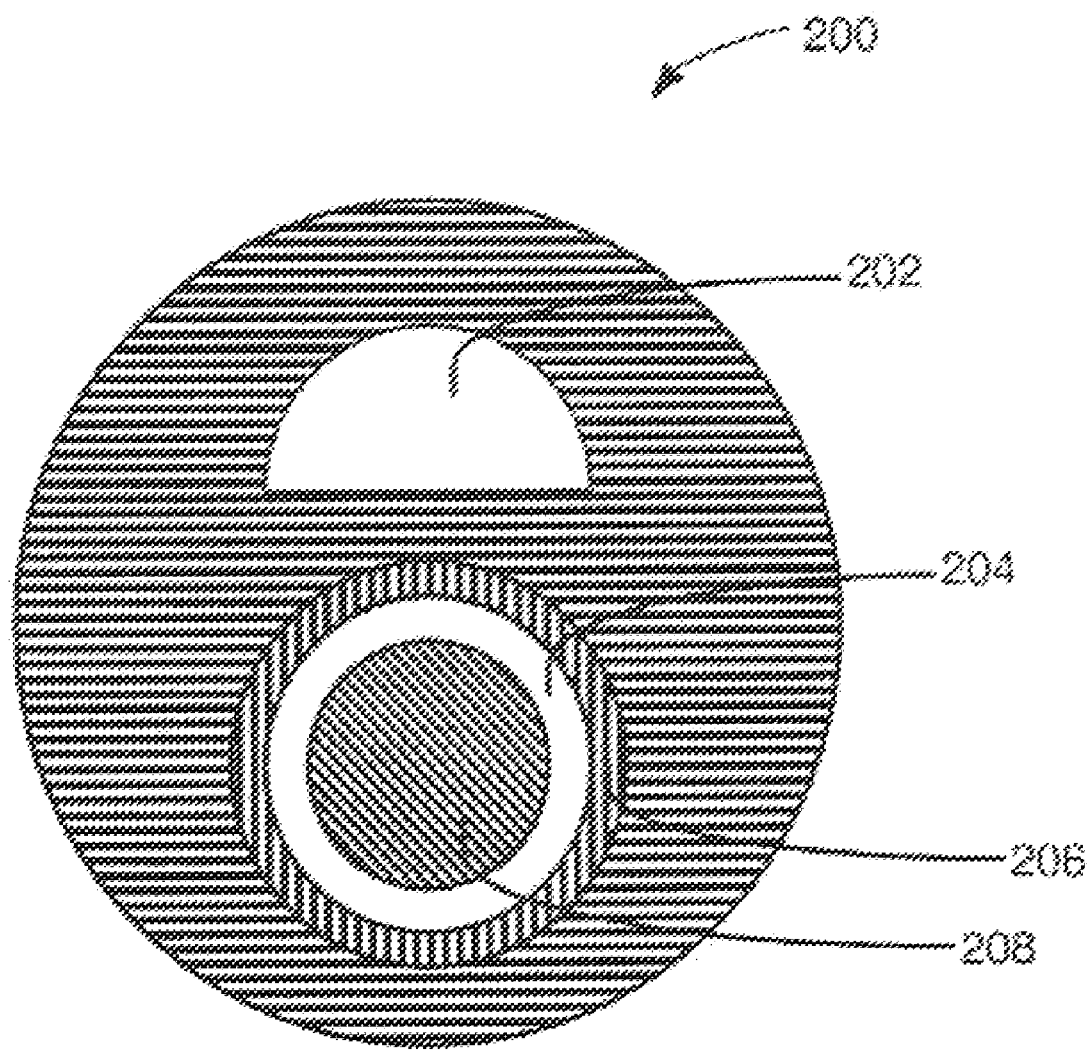
FIG. 2 is a cross-sectional view of a prior art dual lumen non-coaxial catheter.
Figure 3:
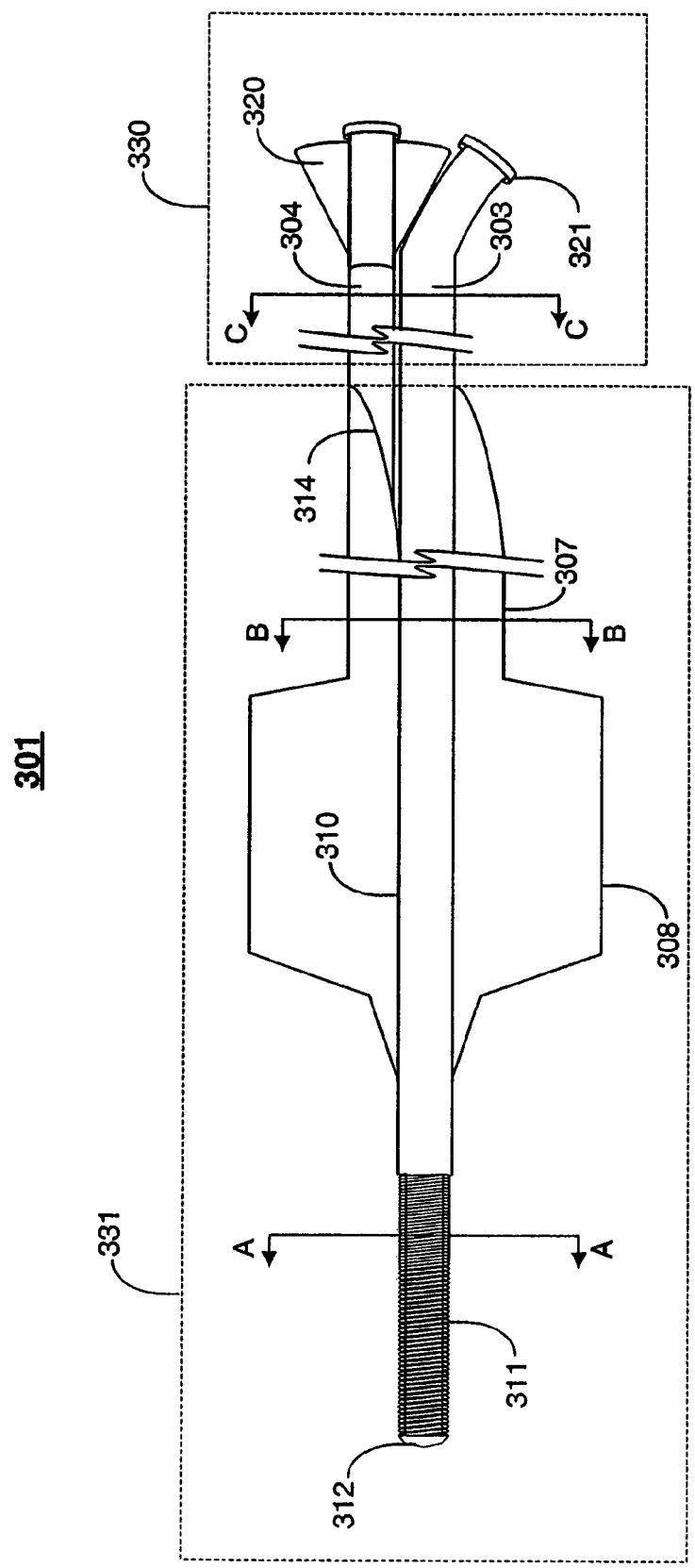
FIG. 3 is a schematic view of a balloon catheter assembly according to the present invention.

Referring first to FIG. 3, an embodiment of a dilatation catheter 301 is shown. Dilatation catheter or balloon catheter 301 includes a proximal portion 330 and a distal portion 331. Proximal portion 330 of catheter 301 includes a luer hub ("inflation luer") 320. Distal portion 331 of catheter 301 includes a dilatation balloon 308. An interior of balloon 308 is in fluid communication with an external source of inflation fluid through an inflation shaft 304. As may be further seen from FIG. 3, distal portion 331 of catheter 301 includes a flexible coil tip 311 and a hemispheric end cap 312.

Catheter 301 includes two shafts (tubular members), a support wire shaft 303 and inflation shaft 304, which are arranged side-by-side substantially along the length of proximal portion 330 and transition to a coaxial arrangement in distal portion 331. The structure of catheter 301 of the present invention may therefore be referred to as a multi-lumen structure. Support wire shaft 303 is hollow and extends distal of balloon 308 to flexible coil tip 311. Support wire shaft 303 is flexible enough to function as a catheter, but stiff enough to act as a guide wire with or without an additional core wire.

In one embodiment, support wire shaft 303 includes a variable pitch spiral cut (helical cut) portion 310 (a hollow inner member) that preferably begins proximal of balloon 308 and ends at flexible coil tip 311. Variable pitch spiral cut portion 310 is described further below with respect to FIGS. 7, 8 and 9–11. Note that spiral cut portion 310 distal of balloon 308 is where having changing stiffness characteristics of catheter 301 (e.g., to make catheter 301 more flexible) is particularly advantageous. In an alternate embodiment shown in FIGS. 7A and 8A, a distal portion of support wire shaft 303a includes a metal wound coil portion 310a that preferably begins proximal of balloon 308 and is provided with a hemispheric end cap 312a to form coil tip 311a at its distal end.

Inflation shaft 304 includes a skive portion 314, where inflation shaft 304 transitions to a distal tubing portion 307, which is coaxial with support wire shaft 303. Skive portion 314 is positioned approximately 25–30 cm proximal of balloon 308, and is about 5–7 cm long. Skive portion 314 provides a transition in stiffness from higher stiffness to lower stiffness moving from proximal to distal direction. Distal tubing portion 307 is coupled to a proximal end of balloon 308.

Figure 16:
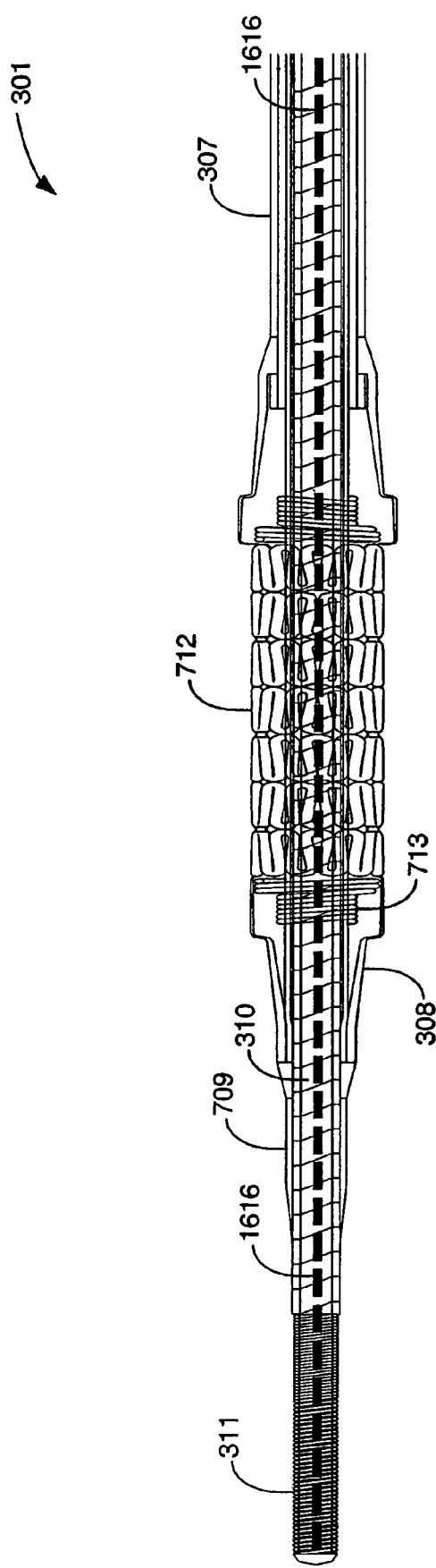
FIG. 16 is a view of FIG. 7 with a core wire inserted.

Further, as shown in FIG. 3, inflation luer 320 includes a wire lock 321. Wire lock 321 is used to lock an inserted core wire in place (not shown in FIG. 3, but see FIG. 16, which shows a core wire (support wire) 1616 inserted in catheter 301) such that the core wire moves with catheter 301, i. e., in tandem with catheter 301.

Support wire shaft 303 is preferably a hypotube throughout its length, but may also be a polymer/polymeric, thus being sufficiently stiff to act as a guidewire. Accordingly, catheter 301 of the present invention is usable without core wire 1616, since it possesses both the necessary flexibility to navigate tortuous arteries, and yet has necessary stiffness and trackability to cross lesions therein. Additionally, support wire shaft 303 is hollow and adapted to have core wire 1616 inserted into it, such that a distal end of core wire 1616 extends through balloon 308 to flexible coil tip 311, thereby traversing an interior of balloon 308 through support wire shaft 303.

Figure 7:
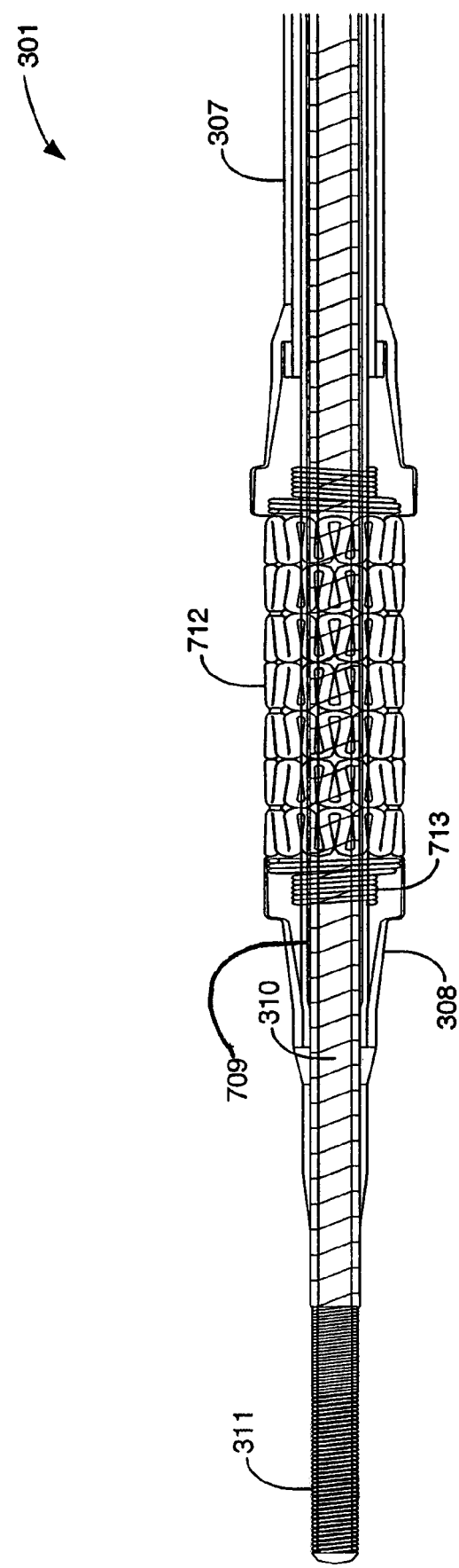
FIG. 7 is an expanded view of a distal portion of the catheter of the present invention.
Figure 7A:
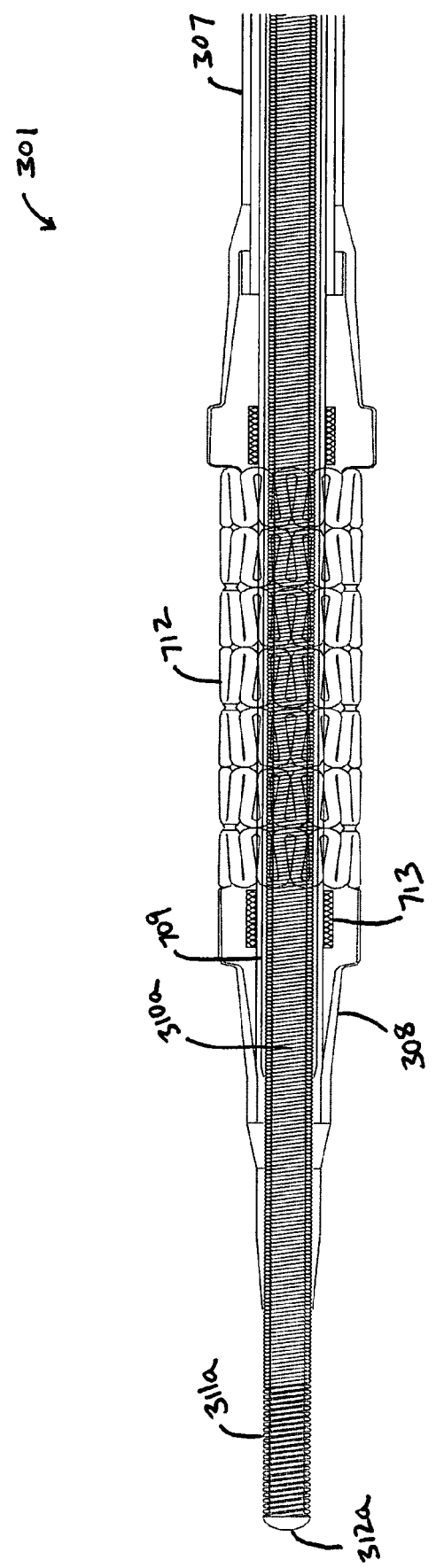
FIG. 7A is an expanded view of an alternate embodiment of a distal portion of the catheter of the present invention.

Flexible coil tip 311 is typically hollow, and in one embodiment is welded to a distal end of variable pitch spiral cut portion 310 of support wire shaft 303 so that core wire 1616 may be advanced therethrough to end cap 312 (see also FIGS. 20–21 and corresponding discussion below). In another embodiment, as shown in FIG. 7A, flexible coil tip 311a is attached to wound coil portion 310a of support wire shaft 303a. In either embodiment, an optional recess may be provided in a distal portion of support wire shaft 303 or 303a to facilitate the welding of coil tip 311 or 311a thereto. End cap 312 and 312a are typically roughly hemispherical in shape.

Both support wire shaft 303 and inflation shaft 304 may be hypotubes, made of surgical grade stainless steel, such as No.304 or No.316. Alternatively, both or either may be made of polymeric materials, such as polyamide, Grilamide or PEEK. Alternatively still, both or either may be made of a composite metal-polymer material. Generally, the selection of the material will depend on the degree of stiffness desired and the dimensions and wall thickness needed, particularly from support wire shaft 303. Both support wire shaft 303 and inflation shaft 304 can be manufactured using a metal extrusion process or a polymer extrusion process. Inflation shaft 304 can also be made from such materials as AESN, and polymeric materials including silicone rubber, polypropylene, polyethylene, polyvinylchloride, fluoropolymers and the like or other dielectric materials, as would be apparent to one skilled in the relevant art.

Inflation shaft 304 is in fluid communication with balloon 308, and is used to inflate and deflate balloon 308. After balloon catheter 301 is properly positioned in a blood vessel, an inflation fluid is forced through inflation shaft 304 to inflate balloon 308, forcing balloon 308 to expand against the interior of the blood vessel. After expansion, balloon 308 is deflated through the same inflation shaft 304 used for inflation, and catheter 301 is withdrawn.

Balloon 308 is formed of a thin pliable material capable of expanding from a compact, collapsed state to an expanded diameter. Balloon 308 may be formed from polyethylene teraphthalate (PET) and exhibit the desirable properties of high burst strength and relatively low radial expansion when inflated to high pressures. Alternatively, balloon 308 may be formed from polyethylene, polypropylene, polyvinyl chloride or other material, as would be apparent to one skilled in the relevant art. Balloon 308 is approximately 2–4 cm long and is attachable to distal portion 331 of catheter 301 by methods known in the art, including gluing, melting or welding.

Figure 4:
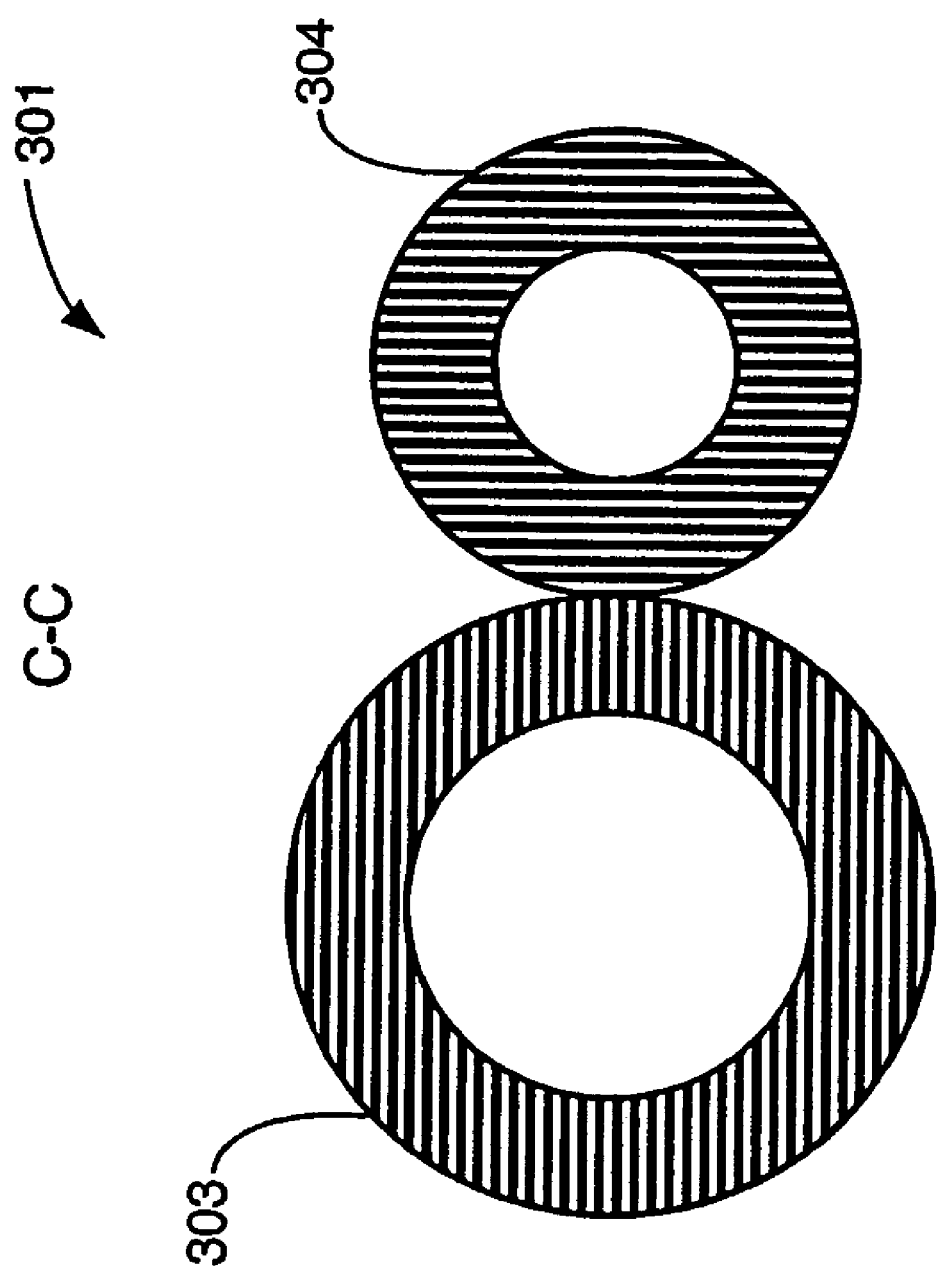
FIG. 4 is a cross-section of an embodiment of a proximal catheter shaft according to the present invention across line C—C of FIG. 3.

FIG. 4 illustrates a cross-section across line C—C of FIG. 3. As shown in FIG. 4, catheter 301 of the present invention includes the two shafts side-by-side, support wire shaft 303 and inflation shaft 304. It will be appreciated that although inflation shaft 304 is shown as being smaller in diameter then support wire shaft 303, this need not be the case. Generally, inflation shaft 304 needs to have a diameter such that balloon 308 can be deflated in approximately 10–15 seconds. At the same time, there is market demand for catheters with low profiles. Similarly, the dimensions of support wire shaft 303 are sufficient for core wire 1616 to fit within and slide through support wire shaft 303. Core wire 1616 does not need to be as big in diameter as conventional guide wires. Support wire shaft 303 should be slightly larger in diameter than core wire 1616, for example, by about 0.001 to 0.005 inches.

Figure 5:
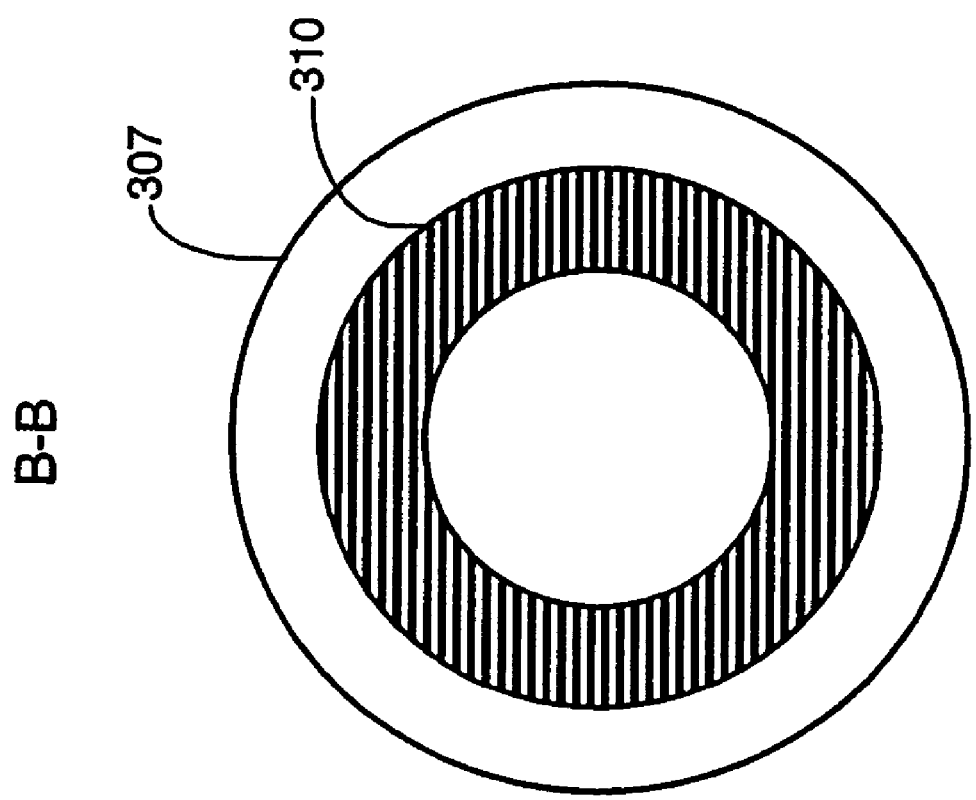
FIG. 5 is a cross-section across line B—B of FIG. 3.
Figure 8:
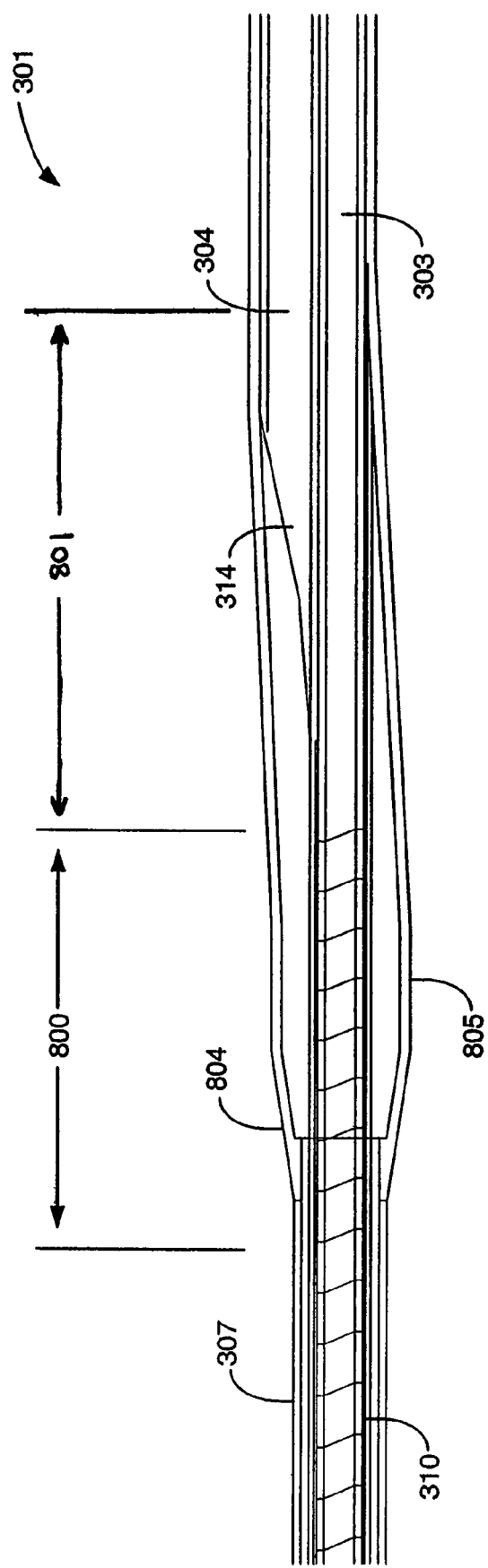
FIG. 8 is an expanded view of a transition area proximal of a balloon of the catheter of FIG. 7.

FIG. 5 shows a cross-section across line B—B of FIG. 3. With reference to FIGS. 7 and 8, support wire shaft 303 in distal portion 331 just proximal of, within and distal of balloon 308 includes spiral cut portion 310 that acts to increase the flexibility of support wire shaft 303.

Figure 6:
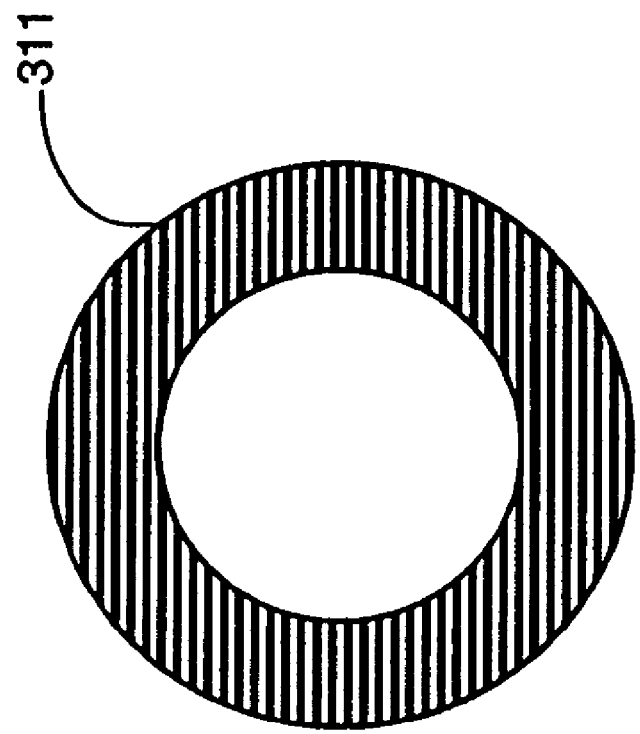
FIG. 6 is a cross-section across line A—A of FIG. 3.

FIG. 6 shows a cross-section of FIG. 3 across line A—A, which illustrates a cross-section of flexible coil tip 311 of catheter 301 of the present invention. With reference to FIGS. 7 and 8, an outer diameter of flexible coil tip 311 is generally comparable to an outer diameter of spiral cut portion 310 of support wire shaft 303. Flexible coil tip 311 is typically made from a small diameter steel wire, such as no. 304 or 316 grade stainless steel wire, and is wrapped around a mandril into the shape shown in FIGS. 7 and 9. Other possible materials for flexible coil tip 311 include Nitinol, MP35N and other nickel alloys. Flexible coil tip 311 is the most flexible part of catheter 301. Coil tip 311 terminates with the (roughly) hemispheric end cap 312.

FIGS. 7 and 8 show an enlarged view of distal portion 331 of catheter 301 of the present invention. As may be seen from FIGS. 7 and 8, moving from a proximal position to a distal position, catheter 301 of the present invention includes inflation shaft 304 and support wire shaft 303, which are positioned substantially side-by-side (generally adjacent to each other). In skive portion 314, inflation shaft 304 gradually transitions to a transition tube 805, in an intermediate transition bond area 800 of catheter 301. Transition tube 805 is typically more flexible than inflation shaft 304. Transition tube 805 is bonded to distal tubing portion 307 with a transition bond (joint) 804. Distal tubing portion 307 is typically made of a polymeric material, such as PEBAX, Nylon or polyester.

Figure 10:
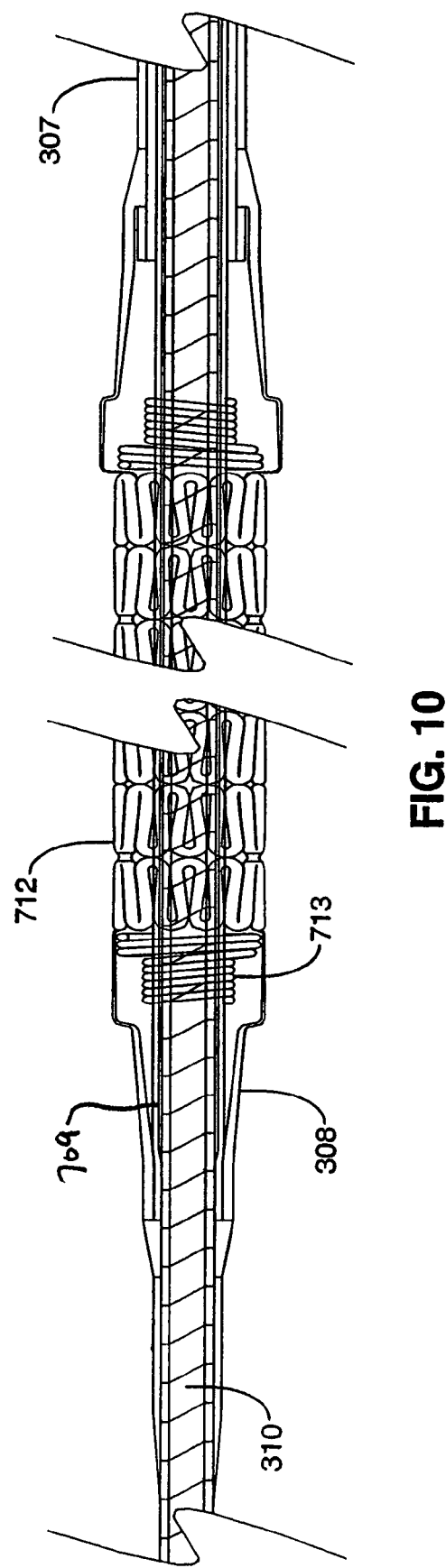
FIG. 10 is an expanded view of a balloon portion of the catheter of the present invention.
Figure 12:
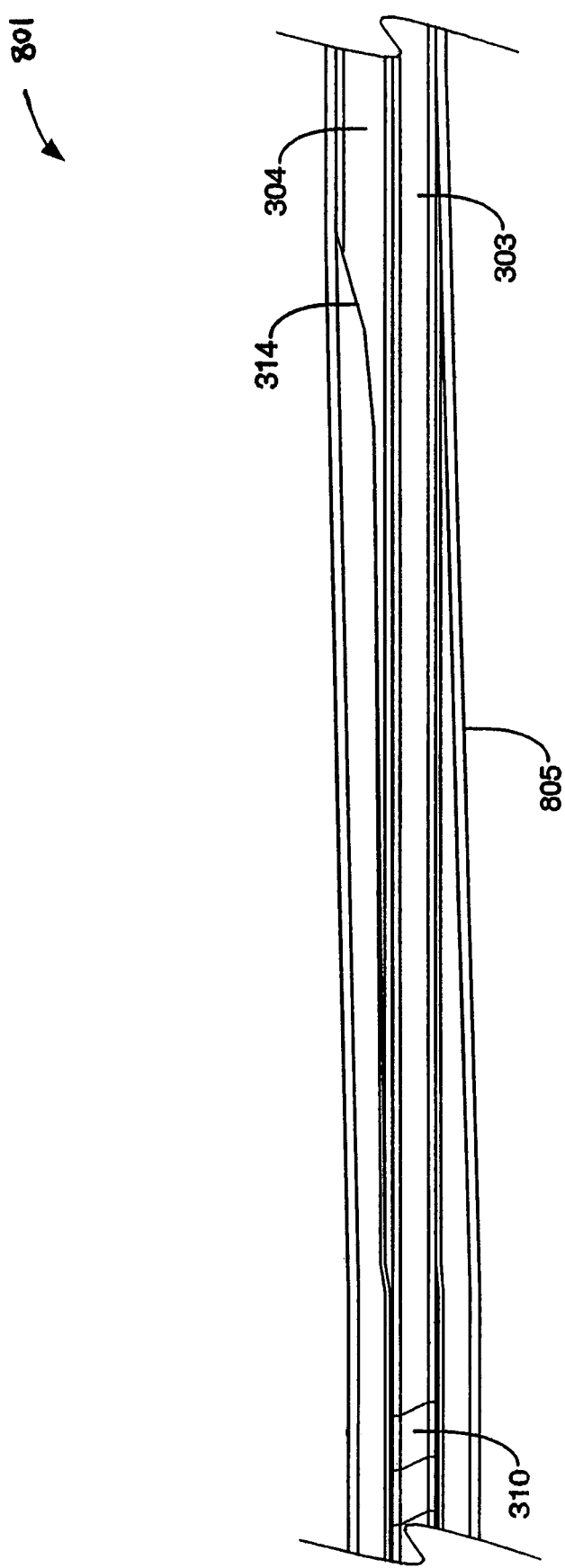
FIG. 12 is an expanded area of a skive portion area of the catheter of the present invention.

Transition bond 804 joins transition tube 805 to distal tubing portion 307. (See also FIG. 12 illustrating the conversion bond area in greater detail.) Distal tubing portion 307 is in fluid communication with balloon 308 for inflation. Support wire shaft 303 extends through and distal of balloon 308 to coil tip 311. In FIG. 7, a stent 712 is shown mounted on balloon 308. An overjacket 709 covers support wire shaft 303 distal of balloon 308 (and optionally covers the entire spiral cut portion 310 of support wire shaft 303). Overjacket 709 may be made of a polymer, such as Nylon (polyamide), PEBAX® polyether block amide, or polyester-based polymers. An optional radiopaque marker 713 is also shown in FIGS. 7 and 10.

As discussed above, support wire shaft 303 includes spiral cut portion 310, such that the spiral cut begins approximately around skive portion 314 (see also FIG. 8), and ends at coil tip 311. The pitch of the spiral cut gradually decreases as one moves in direction from proximal to distal. For example, in one embodiment, the pitch of the spiral cut is approximately 1 mm where the spiral cut begins near skive portion 314, and reduces to approximately 0.25 mm at the spiral coil tip 311, i.e., a factor of 4. The gradual decrease in the pitch of the spiral cut allows for a gradual (i.e., continuous) transition in flexibility in direction from proximal to distal.

Figure 9:
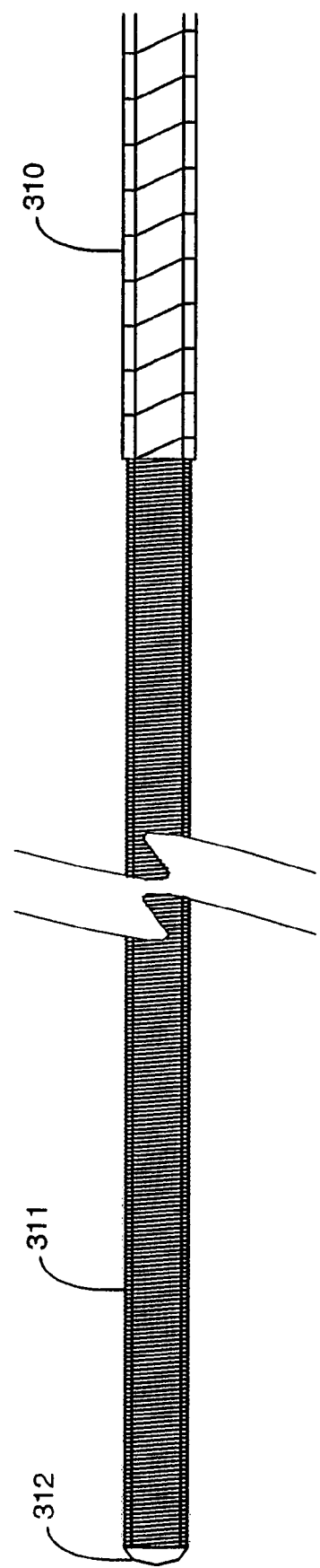
FIG. 9 is an expanded view of a coil tip of the catheter of the present invention.

FIG. 9 further illustrates distal portion 331 of catheter 301 of the present invention. As shown in FIG. 9, spiral cut portion 310 is coupled to flexible coil tip 311, for example, by welding. As noted above, a recess may be formed in the distal portion of spiral cut portion 310 of support wire shaft 303 to enable better coupling between the distal portion of spiral cut portion 310 and flexible coil tip 311.

Figure 20:
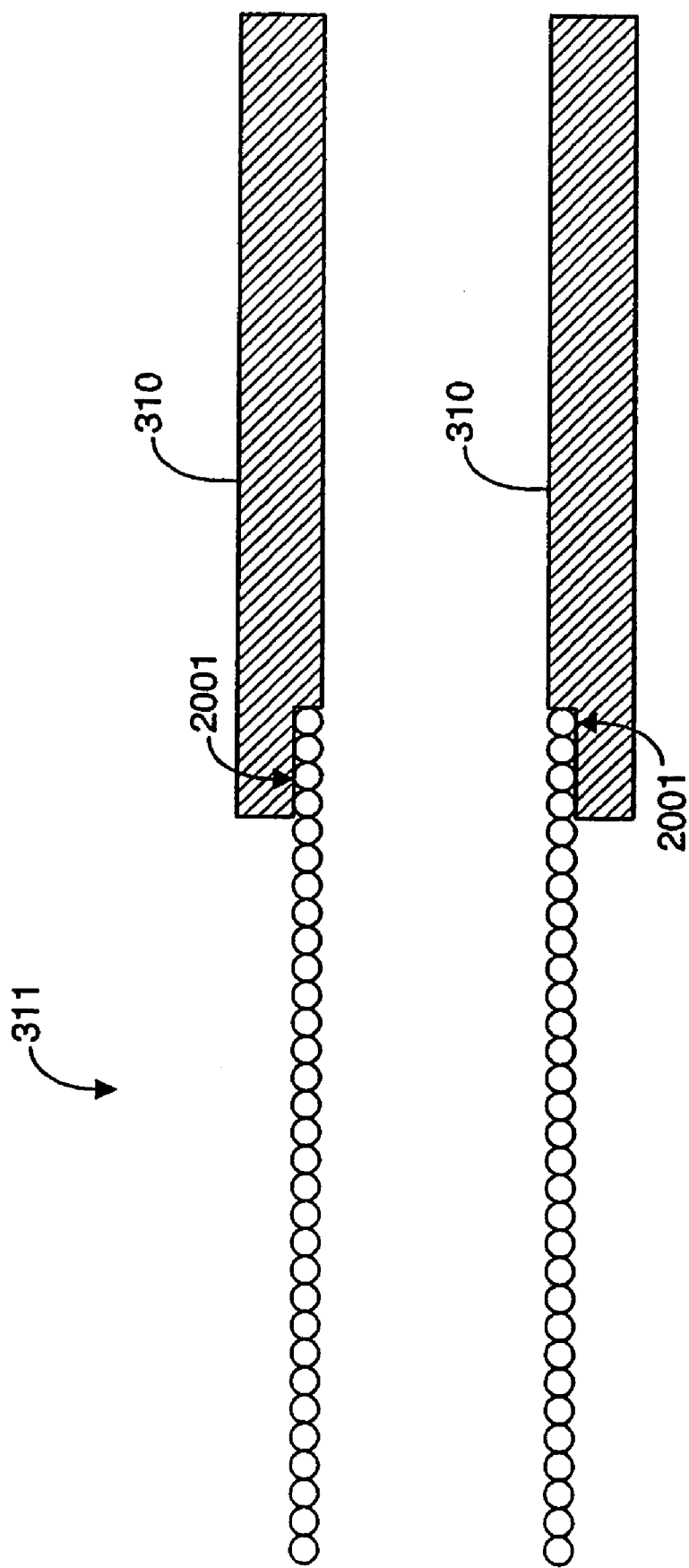
FIG. 20 shows a cross-section of a coil tip and hypotube joint of the present invention.

FIG. 20 shows a cross-section of one way to couple coil tip 311 and spiral cut portion 310 of support wire shaft 303. Coil tip 311 is typically made from a wire 0.002 to 0.004 inches in diameter. Spiral cut portion 310 may have a wall thickness from about 0.002 inches to 0.007 inches. To couple coil tip 311 to spiral cut portion 310, a recess 2001 is provided in support wire shaft 303. Note that a reverse of this approach may also be utilized to insure a constant outer diameter between spiral cut portion 310 of support wire shaft 303 and coil tip 311.

Figure 21:
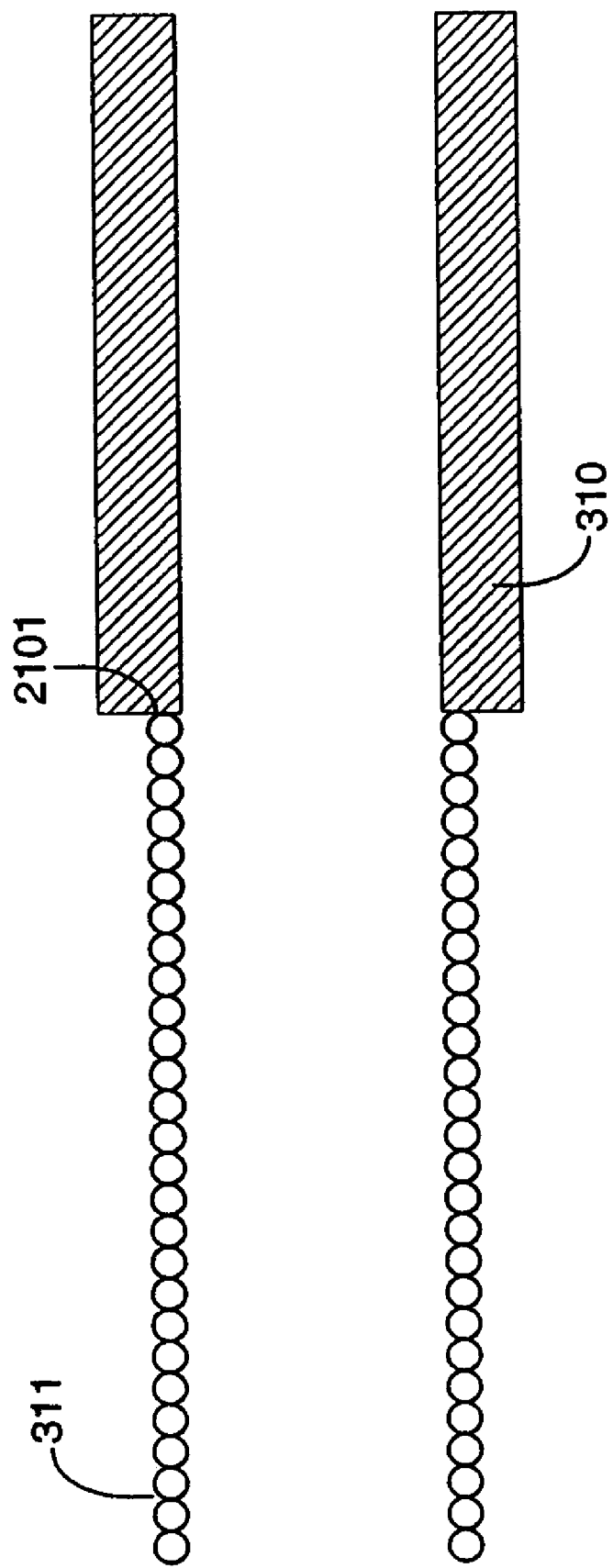
FIG. 21 shows a cross-section of a butt joint of the hypotube and coil tip of the present invention.

FIG. 21 illustrates a cross-section of how a simple butt joint 2101 can be used to couple spiral cut portion 310 and coil tip 311.

FIG. 10 illustrates additional detail of the balloon portion of catheter 301. As shown in FIG. 10, the balloon portion includes distal tubing portion 307, which is fluidly coupled to balloon 308. Spiral cut portion 310 is shown as passing through the interior of balloon 308, and, as noted above, is hollow to enable core wire 1616, inserted into support wire shaft 303, to reach coil tip 311. FIG. 10 also shows polymer overjacket 709 on spiral cut portion 310.

Figure 11:
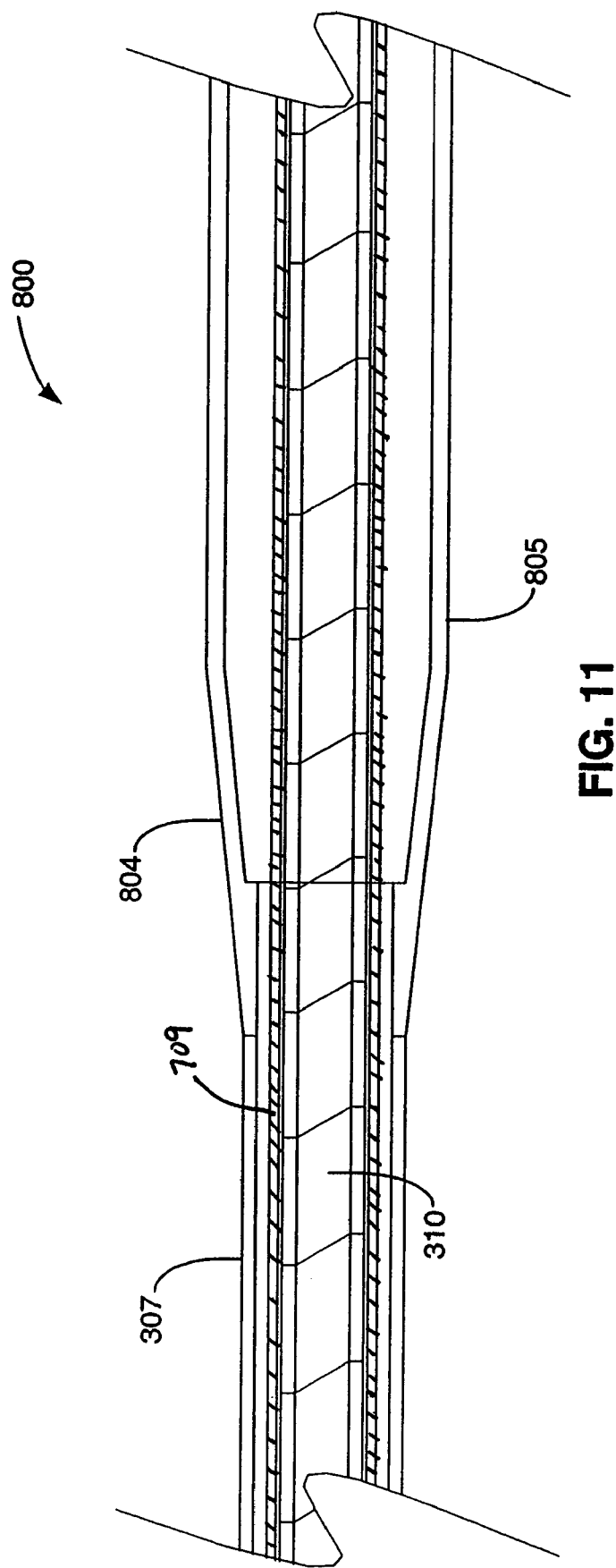
FIG. 11 is an expanded view of an intermediate bond area of the catheter of the present invention.

FIG. 11 is an expanded view of intermediate bond area 800 of catheter 301 of the present invention as shown in FIG. 8. As may be seen from FIG. 11, intermediate bond area 800 includes transition tube 805, distal tubing portion 307, transitionbond 804, and spiral cutportion 310 that includes overjacket 709. Note that overjacket 709 may be placed around the entire spiral cut portion 310 in order to seal it, so as to maintain inflation pressure and prevent leaks. Furthermore, balloon 308 may be thermally bonded to overjacket 709.

FIG. 12 illustrates an expanded view of a conversion bond area 801 of catheter 301 of the present invention, as shown in FIG. 8. As shown in FIG. 12, support wire shaft 303 is side-by-side with inflation shaft 304 proximal of skive portion 314. Transition tube 805 provides fluid communication between skive portion 314 of inflation shaft 304 and distal tubing portion 307 (as shown in FIG. 11). Spiral cut portion 310 of support wire shaft 303 begins just distal of skive portion 314 and is coaxial with transition tube 805.

Figure 8A:
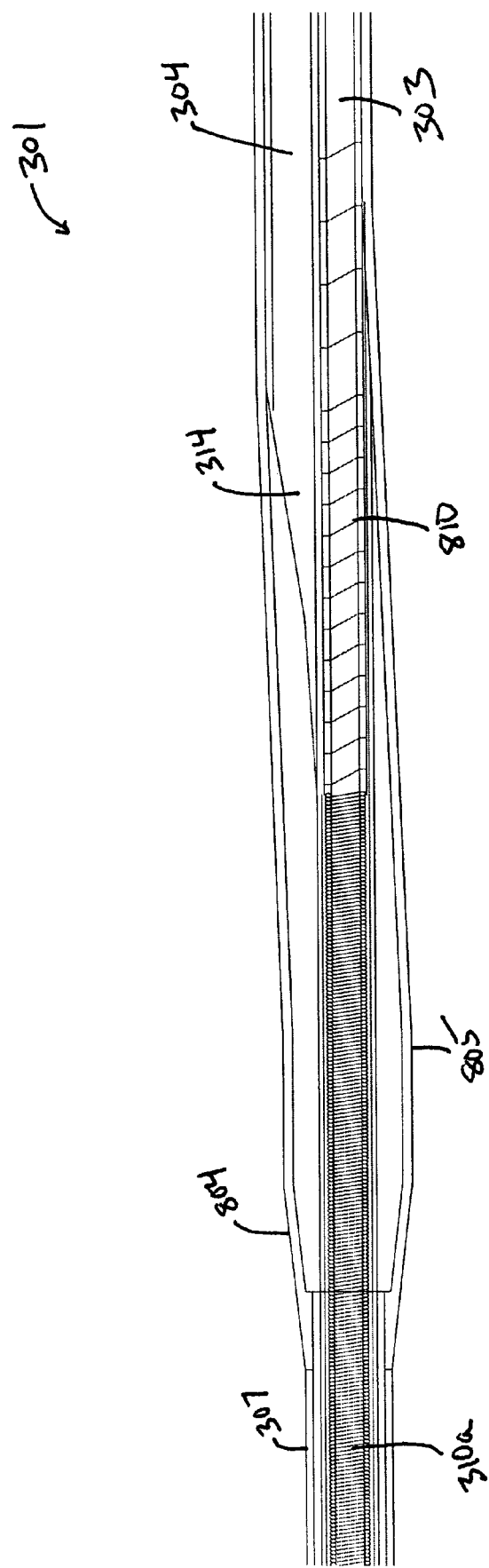
FIG. 8A is an expanded view of a transition area proximal of a balloon of the catheter of FIG. 7A.

FIGS. 7A and 8A show an enlarged view of an alternate embodiment of distal portion 331 of catheter 301 of the present invention. FIG. 8A shows the transition from the more flexible distal end of the catheter to the more rigid proximal end. As described above with respect to FIGS. 7 and 8, catheter 301 of the present invention includes inflation shaft 304 and support wire shaft 303, which are positioned substantially side-by-side (generally adjacent to each other). In the embodiment shown in FIG. 8A, a spiral cut 810 in a distal end of support wire shaft 303 provides a transition in flexibility into wound coil portion 310a, while an adjacent hypotube forms inflation shaft 304.

Inflation shaft 304 includes a skive portion 314, where inflation shaft 304 transitions to a distal tubing portion 307, which is coaxial with support wire shaft 303. In skive portion 314, inflation shaft 304 gradually transitions to a transition tube 805, in an intermediate transition bond area 800 of catheter 301. Transition tube 805 is typically more flexible than inflation shaft 304. Transition tube 805 is bonded to distal tubing portion 307 with a transition bond (joint) 804. Distal tubing portion 307 is typically made of a polymeric material, such as Nylon (polyamide), PEBAX® polyether block amide, or polyester. Skive portion 314 is positioned approximately 25–30 cm proximal of balloon 308, and is about 5–7 cm long. Skive portion 314 provides a transition in stiffness from stiffness to lower stiffness moving from proximal to distal direction and a tapered transition on the outer diameter of the catheter shaft. Distal tubing portion 307 is coupled to a proximal end of balloon 308. Transition bond 804 joins transition tube 805 to distal tubing portion 307. Distal tubing portion 307 forms the distal portion of the inflation lumen which is in fluid communication with balloon 308 for inflation.

Spiral cut 810 at the distal end of support wire shaft 303 provides a more gradual transition from the rigid proximal end of support wire shaft 303 to the flexible spiral of wound coil portion 310a. Alternatively, a wound coil, similar to wound coil portion 310a, could be used for the entire length of the catheter, eliminating the need for spiral cutting the distal end of support wire shaft 303. However, an entirely wound coil construction may not provide enough support for the proximal end of support wire shaft 303.

Wound coil portion 310a extends through and distal of balloon 308 to coil tip 311a. In FIG. 7A, a stent 712 is shown mounted on balloon 308. An overjacket 709 is provided on metal wound coil portion 310a to seal wound coil portion 310a and maintain inflation pressure within the inflation lumen 304 and balloon 308. Furthermore, balloon 308 may be thermally bonded to overjacket 709. Overjacket 709 may be made of a polymer, such as Nylon (polyamide), PEBAX® polyether block amide, or polyester-based polymers. Wound coil portion 310a preferably extends beyond the distal end of overjacket 709, leaving bare wire, creating a guidewire like distal tip 311a. In one embodiment of the present invention, wound coil portion 31310a extends beyond overjacket 709 by 5 cm to 10 cm. An optional radiopaque at marker 713 is also shown in FIG. 7A.

As discussed above, wound coil portion 310a begins just distal of skive portion 314, as shown in FIG. 8A, and is coaxial with transition tube 805. Preferably, the distal 10 cm to 30 cm of support wire shaft 303 are supported with wound coil portion 310a. Wound coil portion 310a is provided with an end cap 312a to form coil tip 311a. Endcap 312a is preferably roughly hemispherical in shape. Wound coil portion 310a is shown in FIG. 7A as passing through the interior of balloon 308, and is hollow to enable core wire 1616, inserted into support wire shaft 303, to reach coil tip 311a. The flexibility characteristics of wound coil portion 310a can be controlled by varying the pitch of the coil and the thickness of the wire or ribbon it is made from, as would be apparent to one of ordinary skill in the art.

An inner member similar to wound coil portion 310a and overjacket 709 could also be constructed for use in a rapid exchange catheter design (not shown), such as that described in U.S. Pat. No. 6,190,358, to Fitzmaurice et al., incorporated herein by reference. However, in such a construction, a spiral cut hypotube, such as the proximal portion of support wire shaft 303, would not be necessary. The wound coil portion 310a would terminate proximally at the wire exchange port, about 25 cm to 35 cm proximal of the balloon, as would be apparent to one of ordinary skill in the art.

Figure 13:
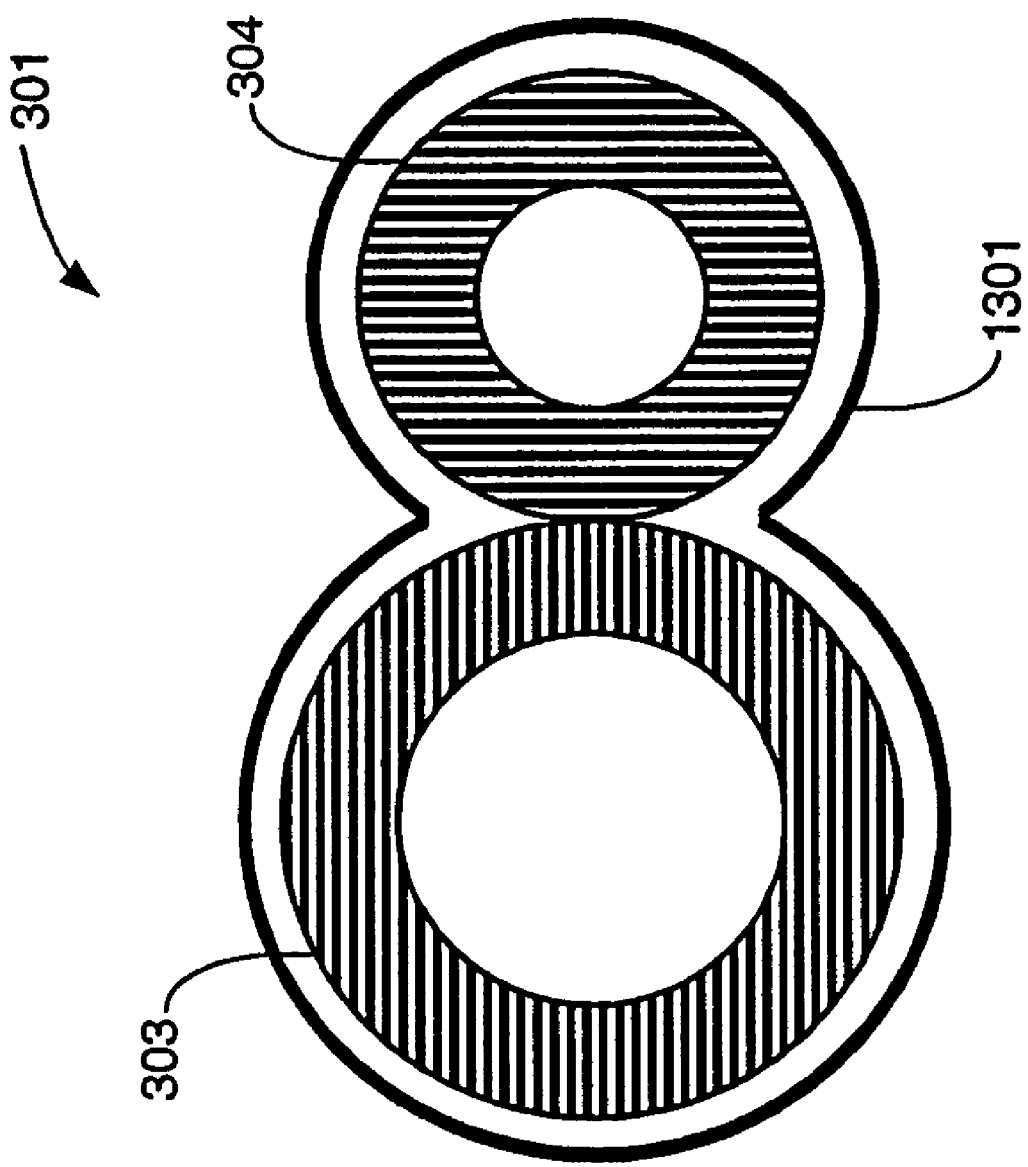
FIG. 13 illustrates a cross-section of another embodiment of a proximal catheter shaft of the present invention across line C—C of FIG. 3 with an overjacket shown.

FIG. 13 illustrates a cross-section of another embodiment of a proximal catheter shaft according to the present invention across line C—C of FIG. 3. Specifically, FIG. 13 illustrates a jacket 1301 surrounding support wire shaft 303 and inflation shaft 304. Jacket 1301 maybe used to couple (bond) support wire shaft 303 and inflation shaft 304 together, throughout proximal portion 330 of catheter 301 For example, for an approximately 100–135 cm long catheter 301, jacket 1301 preferably extends for approximately 70–80% of its proximal length. It is anticipated that even if the coupling were to extend for a much smaller portion, for example, 5–10 cm, the coupling effect provided is still beneficial to the user in terms of added torquability and steerability.

Other methods of bonding support wire shaft 303 and inflation shaft 304 may be used. For example, the two shafts 303, 304 may be welded together throughout a substantial portion of their lengths. Alternatively, they may be welded together only in selected portions, for example, the proximal 5–10 cm. Shafts 303, 304 may be epoxied or glued together. Shafts 303, 304 may also be coupled together using a plurality of "ties."

Figure 15:
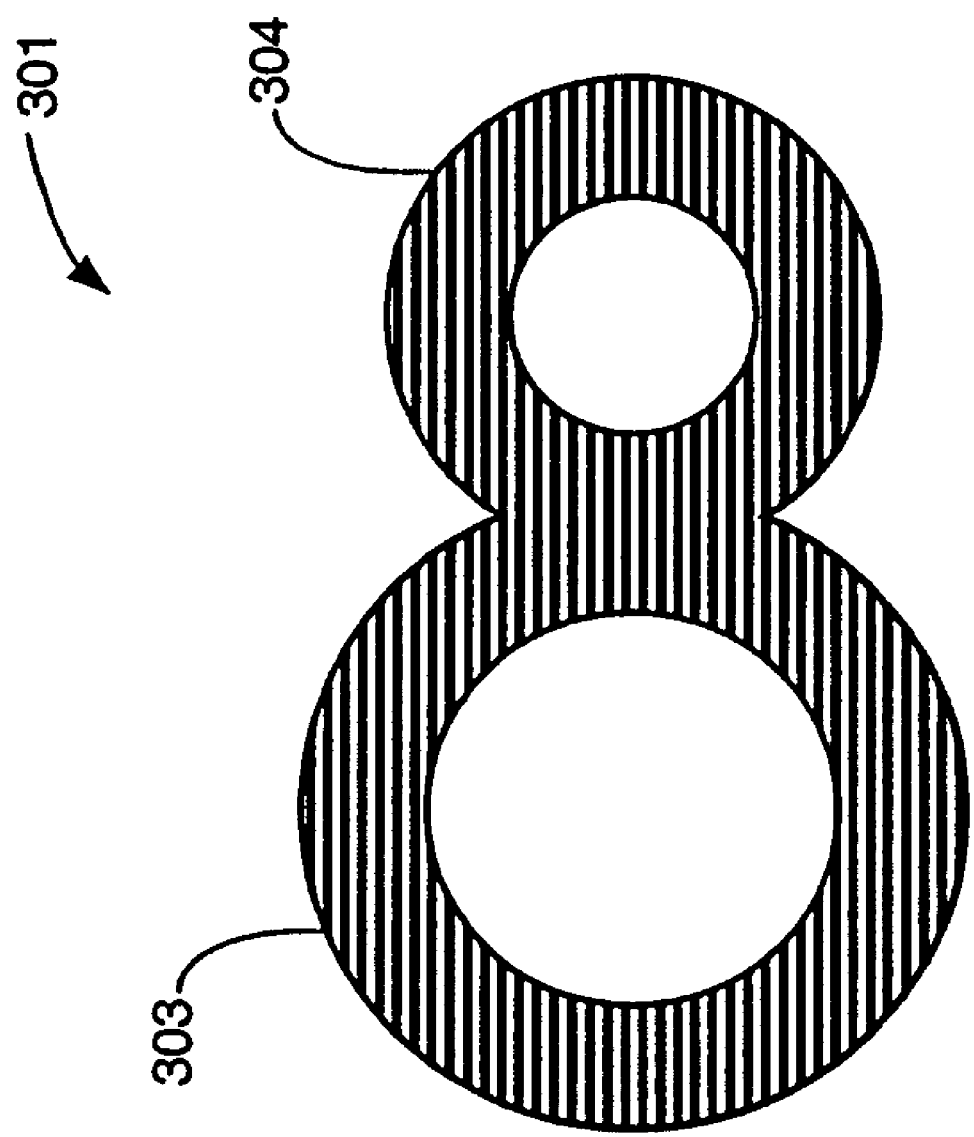
FIG. 15 illustrates a cross-section of another embodiment of a proximal catheter shaft according to the present invention across line C—C of FIG. 3 illustrating integrally formed shafts.

Another embodiment of a proximal catheter shaft according to the present invention includes extruding shafts 303, 304 together as an integrated unit, as shown in FIG. 15. Yet another option includes extruding shafts 303, 304 separately, bringing them in contact, and laser fusing (or laser welding) them together.

Figure 14:
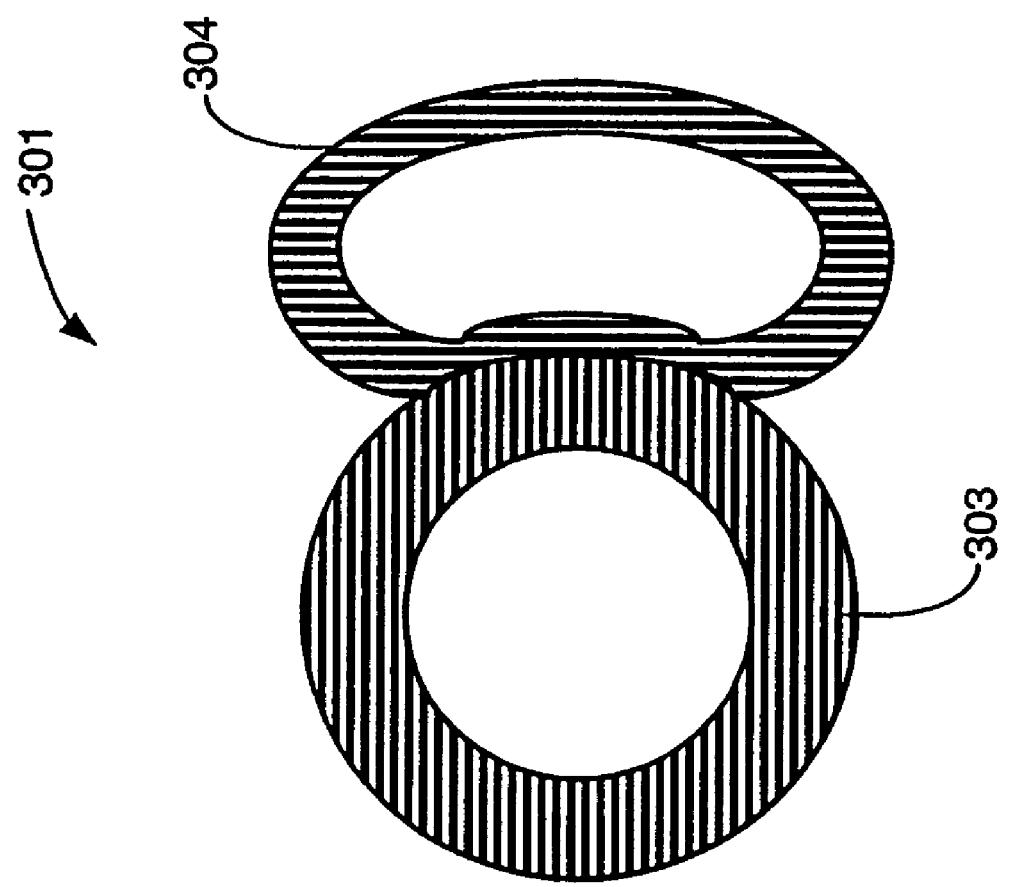
FIG. 14 illustrates a cross-section of another embodiment of a proximal catheter shaft according to the present invention across line C—C of FIG. 3 illustrating an alternative inflation shaft shape.

FIG. 14 illustrates a cross-section of another embodiment of a proximal catheter shaft according to the present invention across line C—C of FIG. 3 illustrating an alternative shape of inflation shaft 304. As noted above, the market continues to demand ever lower catheter profiles. Accordingly, inflation shaft 304 is formed to correspond to an outer surface of support wire shaft 303, so as to create a "crescent" shape. Other cross-sectional shapes of inflation shaft 304 may include a substantially D-shape, such that an overall profile of catheter 301 is reduced.

Although in the embodiment described above, the conversion bond area shown in FIG. 12 includes transition tube 805 between inflation shaft 304 and distal tubing portion 307, with the distal tubing portion 307 fluidly coupled to balloon 308, alternatively, inflation shaft 304 may extend to balloon 308 and be in direct fluid communication with balloon 308 such that transition tube 805 and distal tubing portion 307 are eliminated. Thus, one piece of tubing would extend from the proximal end of the balloon 308 to the inflation luer 320 and wire lock 321. This one piece of tubing may be formed from alternating polymers such that the distal end is pure PEBAX® polyether block amide, the proximal end is pure GRILAMID® Nylon 12, and a mid-section contains layers or a mixture of PEBAX® and GRILAMID®. Other suitable polymers may be used in this manner.

The variable pitch spiral cut of portion 310 of support wire shaft 303 may be accomplished by laser cutting. Portion 310 is positioned in a jig, and advanced forward while the laser forms a thin cut. By varying the speed of the advance, the pitch of the spiral cut portion 310 can gradually transition from a large pitch (more stiff) to a small pitch (more flexible). Alternatively, a blade may be used to form the spiral cut on portion 310. The hypotube may be held in a jig, while a blade, oriented at the required angle, is brought in contact with portion 310 of support wire shaft 303. While portion 310 is rotated and advanced, the blade cuts a spiral slit in portion 310. The use of a blade, rather than a laser, may be more desirable when portion 310 is formed of a polymer, such as GRILAMID® Nylon 12 or polyamide.

As shown in FIG. 3, catheter 301 includes wire lock 321 that is similar to a syringe locking port. Core wire 1616 includes a mating surface, such that it can be screwed on and locked onto luer 320. The mating surface may be nut-like, as discussed below. Other options for holding core wire 1616 fixed relative to catheter 301 include the use of a crimping mechanism on inflation luer 320, or, for example, mechanical jaws that grip core wire 1616.

Figure 17:
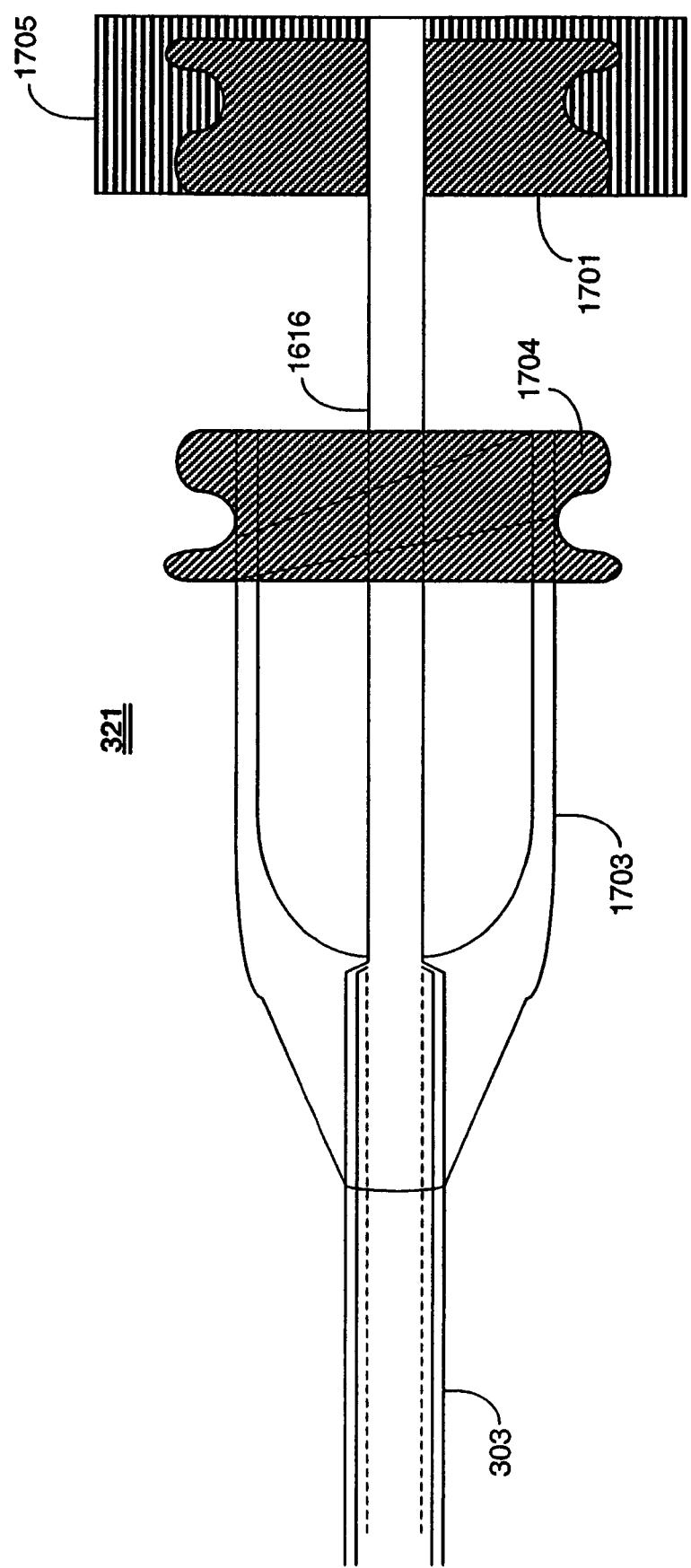
FIG. 17 shows a screw and nut type wire lock mechanism of the present invention.

FIG. 17 shows an example of a screw-and-nut type wire lock mechanism 321 of the present invention. As shown in FIG. 17, support wire shaft 303 terminates in a molded plastic end 1703 having a thread 1704. Note core wire 1616 inserted into support wire shaft 303. A proximal end of core wire 1616 terminates in a nut 1705 that includes a locking cap 1701. Thread 1704 is preferably a standard luer thread commonly used on domestic and international catheter luers. Thread 1704 allows a syringe to be attached to a support wire shaft 303 for flushing it with a saline solution (not shown). Thread 1704 also allows locking cap 1701 to be screwed in place. By engaging locking cap 1701 with thread 1704, the operator secures core wire 1616 to catheter 301, making it an integral part thereof.

Figure 18A:
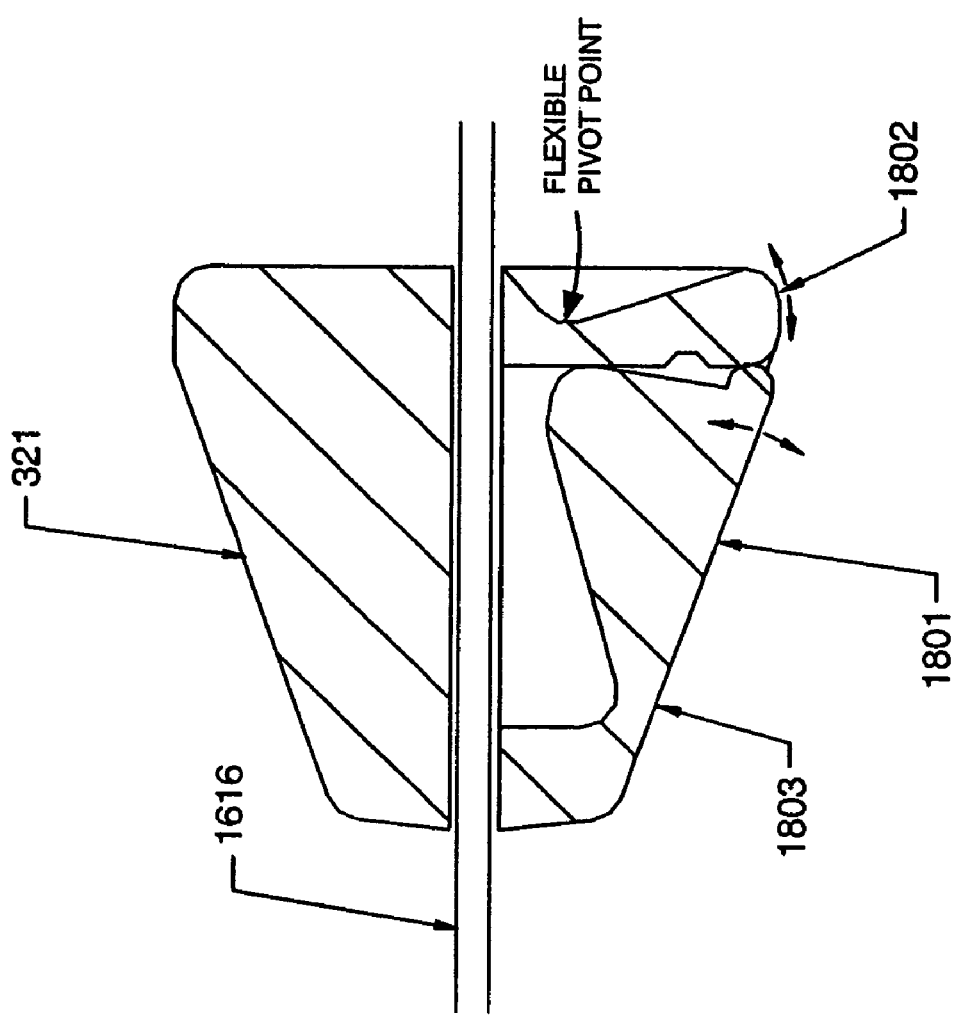
FIGS. 18A–18B show a lever type wire lock mechanism of the present invention.
Figure 18B:
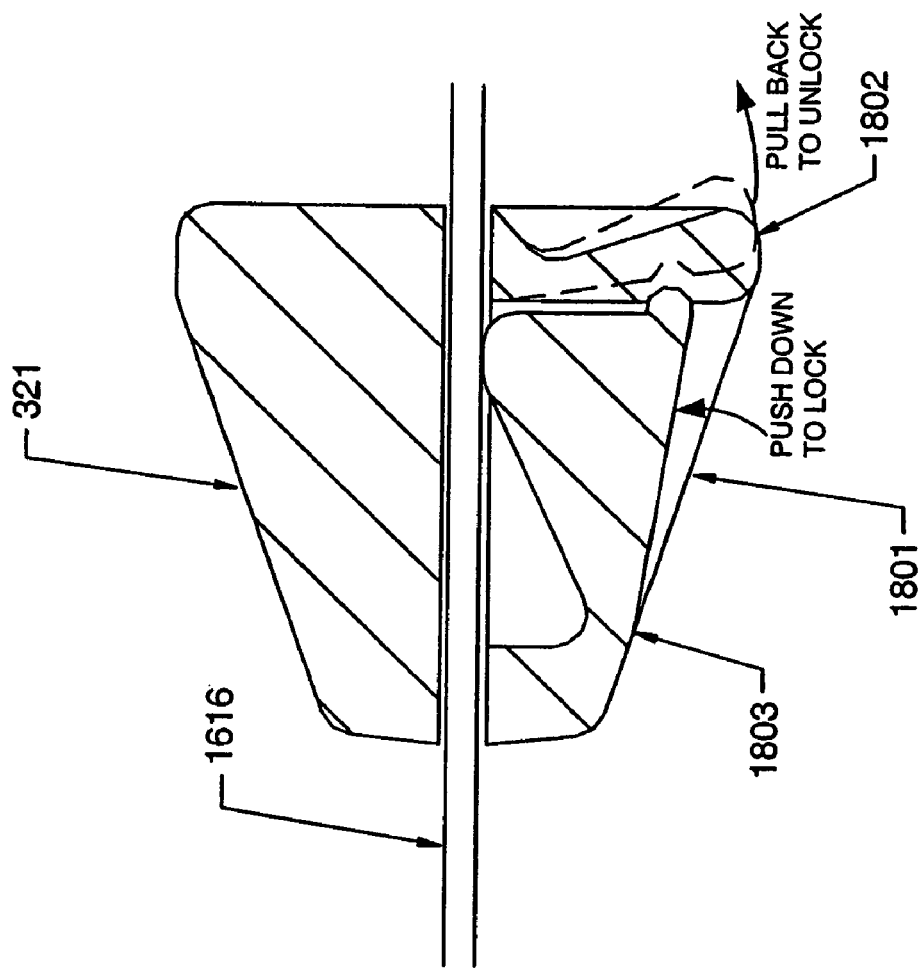

FIGS. 18A–18B show a lever lock type mechanism used as wire lock mechanism 321. As shown in FIGS. 18A–18B, wire lock mechanism 321 includes a locking portion 1801, which is "hinged" at a pivot portion 1803. To lock core wire 1616 in place, locking portion 1801 is pressed down against core wire 1616 until it is secured by a thumb portion 1802. To release core wire 1616, thumb portion 1802 is pushed back. This design allows core wire 1616 to be fixed in place at any point along its length, without necessarily advancing it fully within catheter 301.

Figure 19:
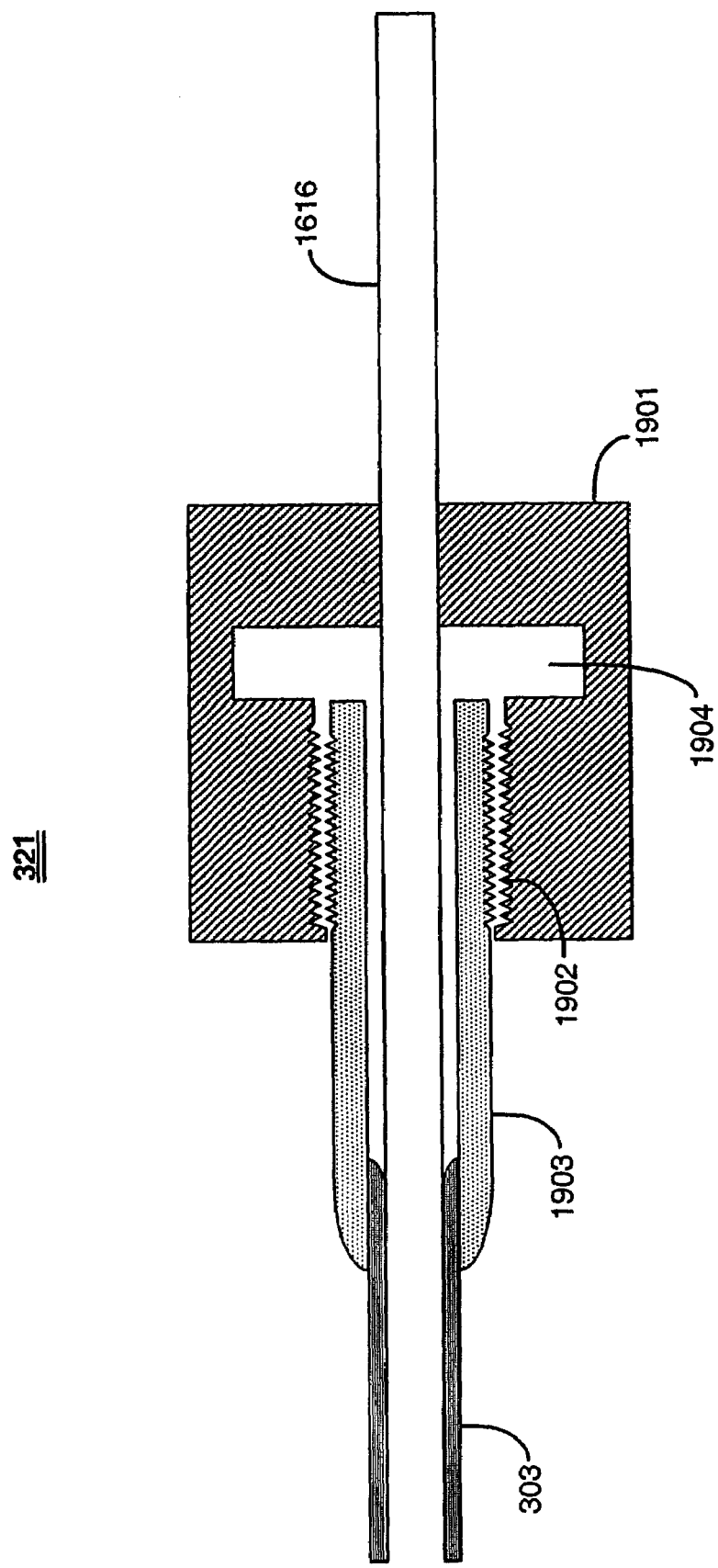
FIG. 19 shows a chuck (or bushing) type wire lock mechanism of the present invention.

FIG. 19 shows a chuck/bushing type wire lock mechanism 321. As shown in FIG. 19, wire lock mechanism 321 includes a female portion 1901, which includes threads 1902, that are coupled to a male portion 1903. Male portion 1903 is in turn coupled to support wire shaft 303. The space 1904 between female portion 1901 and male portion 1903 may include a number of mechanisms, such as a 3-jawed chuck, or a rubber (or polymer) bushing where upon the wire is held in place when the female portion 1901 is tightened over the male portion 1903. Both a 3-jawed chuck mechanism and the rubber or polymer bushing will transfer an axial force into a circumferential force.

Catheter 301 of the present invention allows for greater control of its distal portion 331, and greater steerability. The ability to add core wire 1616 after tracking catheter 301 through a patient's vasculature allows for greater control of the stiffness and other characteristics of catheter 301, such that an operator has greater flexibility during the procedure.

The use of catheter 301 of the present invention in most applications eliminates the extra step of inserting a guide wire, due to the use of a "hollow guide wire", i. e., support wire shaft 303. Further, the present invention allows for interchangeability (replaceability) of a core wire within support wire shaft 303. Catheter 301 of the present invention may be used in coronary, peripheral, and cranial applications.

Figure 22:
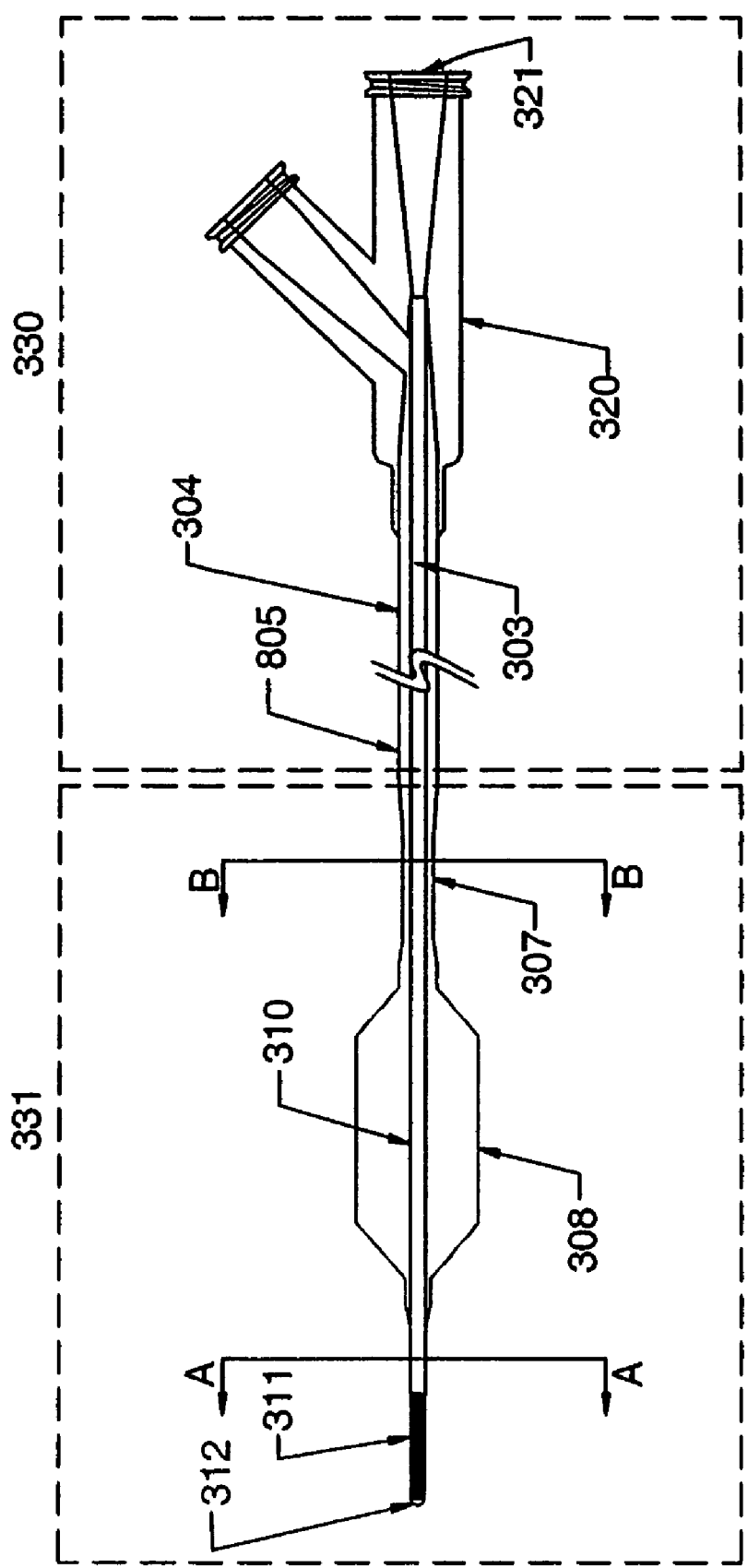
FIG. 22 shows an embodiment of the catheter of the present invention using a coaxial arrangement of inflation shaft and support wire shaft.

FIG. 22 shows an embodiment of the catheter of the present invention using a coaxial arrangement of inflation shaft 304 and support wire shaft 303. Other corresponding elements have been numbered with the same reference numerals as in FIG. 3.

It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A catheter comprising:
a support wire shaft having a distal end and a proximal end and terminating distally in a wound coil portion;
the wound coil portion having a metal coil tip formed at a distal most end of the wound coil portion;
a jacket surrounding at least a portion of the wound coil portion of the support wire shaft;
the metal coil tip having an end cap such that the support wire shaft is terminated at the end cap and a core wire inserted into the support wire shaft cannot be extended distally beyond the distal end of the support wire shaft;
a balloon mounted on a distal portion of the support wire shaft;
an inflation shaft fluidly coupled to the balloon; and
a core wire, wherein the core wire is interchangeably insertable within the support wire shaft when the catheter is within a body lumen; and
wherein the wound coil portion of the support wire shaft extends proximally of the balloon.

2. The catheter of claim 1, wherein the jacket is made of a polymer.

3. A catheter comprising:
a support wire shaft having a distal end and a proximal end and terminating distally in a wound coil portion;
the wound coil portion having a metal coil tip formed at a distal most end of the wound coil portion;
the metal coil tip having an end cap such that the support wire shaft is terminated at the end cap and a core wire inserted into the support wire shaft cannot be extended distally beyond the distal end of the support wire shaft;
a balloon mounted on a distal portion of the support wire shaft;
an inflation shaft fluidly coupled to the balloon; and
a core wire, wherein the core wire is interchangeably insertable within the support wire shaft when the catheter is within a body lumen;
wherein the wound coil portion of the support wire shaft extends proximally of the balloon; and
a proximal portion of the support wire shaft is arranged side-by-side with a proximal portion of the inflation shaft.

4. The catheter of claim 1, wherein the catheter has sufficient stiffness to traverse lesions within a body lumen without the core wire.

5. A catheter comprising:
a support wire shaft having a distal end and a proximal end and terminating distally in a wound coil portion;
the wound coil portion having a metal coil tip formed at a distal most end of the wound coil portion;
the metal coil tip having an end cap such that the support wire shaft is terminated at the end cap and a core wire inserted into the support wire shaft cannot be extended distally beyond the distal end of the support wire shaft;
a balloon mounted on a distal portion of the support wire shaft;
an inflation shaft fluidly coupled to the balloon;
a jacket surrounding and coupling the support wire shaft and the inflation shaft along a majority of their length
a core wire, wherein the core wire is interchangeably insertable within the support wire shaft when the catheter is within a body lumen; and
wherein the wound coil portion of the support wire shaft extends proximally of the balloon.

6. A catheter comprising:

a support wire shaft terminating distally in a wound coil portion;

a balloon mounted on a distal portion of the support wire shaft;

an inflation shaft fluidly coupled to the balloon; and a core wire, wherein the core wire is interchangeably insertable within the support wire shaft when the catheter is within a body lumen, and the core wire cannot extend beyond a distal end of the support wire shaft;

wherein the wound coil portion of the support wire shaft extends proximally of the balloon; and further comprising:

a bifurcated hub coupled to a proximal portion of the support wire shaft and the inflation shaft; and a core wire locking mechanism for coupling the core wire to the bifurcate hub when the core wire is inserted within the support wire shaft.

7. The catheter of claim 6, wherein the core wire locking mechanism includes a nut portion attached to a proximal end of the core wire for engagement with a thread portion secured to a proximal end of the support wire shaft.

* * * * *